US012642441B1

(12) United States Patent
Shah et al.

(10) Patent No.: US 12,642,441 B1
(45) Date of Patent: Jun. 2, 2026

(54) FAST PRESENCE DETECTION (FPD) OF A PERSON BASED ON A BREATHING WAVEFORM

(71) Applicant: Amazon Technologies, Inc., Seattle, WA (US)

(72) Inventors: Kandarp Shah, San Jose, CA (US); Pratik Kalpesh Patel, San Jose, CA (US); Sai Prashanth Chinnapalli, Dublin, CA (US); Zheda Li, Mountain View, CA (US); Durga Laxmi Narayana Swamy Inti, San Jose, CA (US); Suman Suhas Hosmane, Sunnyvale, CA (US)

(73) Assignee: Amazon Technologies, Inc., Seattle, WA (US)

( * ) Notice: Subject to any disclaimer, the term of this patent is extended or adjusted under 35 U.S.C. 154(b) by 802 days.

(21) Appl. No.: 18/100,313

(22) Filed: Jan. 23, 2023

Related U.S. Application Data

(60) Provisional application No. 63/426,698, filed on Nov. 18, 2022.

(51) Int. Cl.
A61B 5/0205 (2006.01)
A61B 5/00 (2006.01)
G01S 13/04 (2006.01)

(52) U.S. Cl.
CPC .......... A61B 5/0205 (2013.01); A61B 5/4806 (2013.01)

(58) Field of Classification Search
CPC ... A61B 5/0205; A61B 5/4806; A61B 5/0816; A61B 5/1118; A61B 5/746; A61B 5/0022; A61B 5/11; A61B 5/0002; A61B 5/08;

A61B 5/7264; A61B 5/7282; A61B 5/4818; A61B 5/4812; A61B 5/4809; A61B 5/0245; A61B 5/4815; A61B 5/113; A61B 5/002; A61B 5/1112; A61B 5/725; A61B 5/721; A61B 5/087; A61B 5/1135;
(Continued)

(56) References Cited

U.S. PATENT DOCUMENTS

2021/0181328 A1 * 6/2021 Hayashi .................. G01S 17/04

FOREIGN PATENT DOCUMENTS

EP          4556944 A1 * 5/2025 ............. A61B 5/113
WO     WO-2011143631 A2 * 11/2011 ............. G01S 13/87
(Continued)

*Primary Examiner* — Brian L Casler
(74) *Attorney, Agent, or Firm* — Eversheds Sutherland (US) LLP

(57) ABSTRACT

Technologies of a device-based Fast Presence Detection (FPD) for a contactless sleep-tracking device are described. One method of a sleep-monitoring device includes receiving radar data from a radar unit. The radar data includes i) first data representing a breathing waveform associated with a user, ii) a first set of range values, and iii) a first set of confidence values associated with the first data. The method determines absolute magnitude values, first infinite impulse response (IIR) values using the first set of range values, and second IIR values using the first set of confidence values. The method determines a first event representing the user located in a first region using the absolute magnitude values and the first and second IIR values. The method sends an indication of the first event to a cloud service that causes one or more devices in the environment to perform one or more actions.

20 Claims, 13 Drawing Sheets

(58) Field of Classification Search
CPC .... A61B 5/1115; A61B 5/1113; A61B 5/1114;
G06F 3/011; G01S 13/04; G01S 13/42;
G01S 13/50; G01S 13/66; G01S 13/58
USPC ..................................................... 600/26, 27
See application file for complete search history.

(56) References Cited

FOREIGN PATENT DOCUMENTS

| WO | WO-2014055755 A1 * | 4/2014 | ........... A61B 5/1118 |
| WO | WO-2020104465 A2 * | 5/2020 | ........... A61B 5/0823 |

* cited by examiner

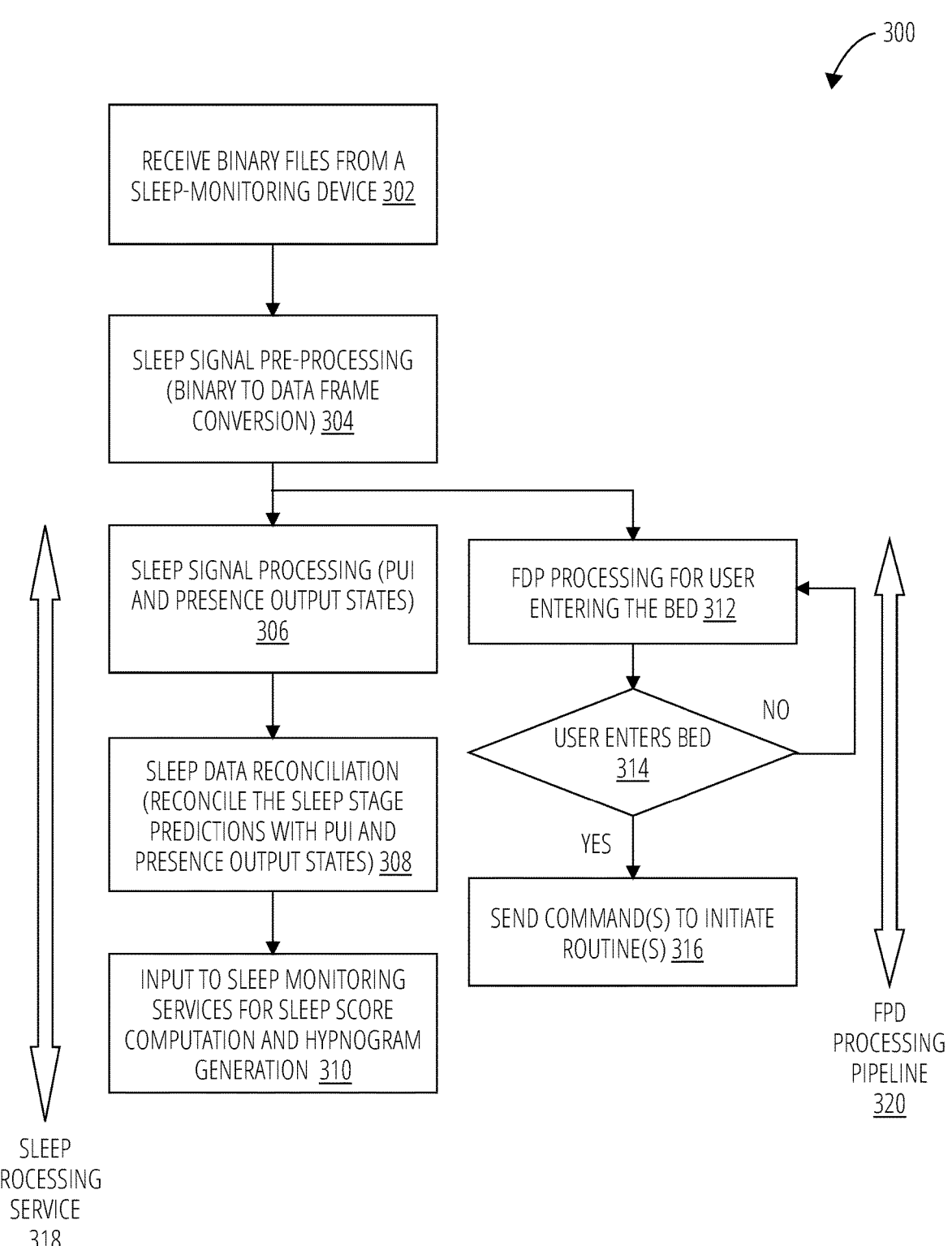

300

RECEIVE BINARY FILES FROM A
SLEEP-MONITORING DEVICE 302

SLEEP SIGNAL PRE-PROCESSING
(BINARY TO DATA FRAME
CONVERSION) 304

SLEEP SIGNAL PROCESSING (PUI
AND PRESENCE OUTPUT STATES)
306

FDP PROCESSING FOR USER
ENTERING THE BED 312

USER ENTERS BED
314

NO

YES

SLEEP DATA RECONCILIATION
(RECONCILE THE SLEEP STAGE
PREDICTIONS WITH PUI AND
PRESENCE OUTPUT STATES) 308

SEND COMMAND(S) TO INITIATE
ROUTINE(S) 316

INPUT TO SLEEP MONITORING
SERVICES FOR SLEEP SCORE
COMPUTATION AND HYPNOGRAM
GENERATION  310

SLEEP
PROCESSING
SERVICE
318

FPD
PROCESSING
PIPELINE
320

FIG. 3

FAST PRESENCE DETECTION ALGORITHM

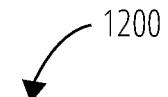

1200

RECEIVE RADAR DATA FROM A RADAR UNIT OF A SLEEP-MONITORING DEVICE, WHEREIN THE RADAR DATA COMPRISES I) FIRST DATA REPRESENTING A BREATHING WAVEFORM ASSOCIATED WITH A USER LOCATED IN AN ENVIRONMENT AROUND THE SLEEP-MONITORING DEVICE, II) A FIRST SET OF RANGE VALUES, EACH RANGE VALUE REPRESENTING A PHYSICAL DISTANCE BETWEEN THE USER AND THE RADAR UNIT, AND III) A FIRST SET OF CONFIDENCE VALUES ASSOCIATED WITH THE FIRST DATA 1202

DETERMINE ABSOLUTE MAGNITUDE VALUES USING THE FIRST DATA 1204

DETERMINE FIRST INFINITE IMPULSE RESPONSE (IIR) VALUES USING THE FIRST SET OF RANGE VALUES 1206

DETERMINE SECOND IIR VALUES USING THE FIRST SET OF CONFIDENCE VALUES  1208

DETERMINE A FIRST EVENT REPRESENTING THE USER LOCATED IN A FIRST REGION OF THE ENVIRONMENT USING THE ABSOLUTE MAGNITUDE VALUES, THE FIRST IIR VALUES, AND THE SECOND FIRST IIR VALUES 1210

SEND A NOTIFICATION OF THE FIRST EVENT TO A CLOUD SERVICES THAT CAUSES THE ONE OR MORE DEVICES TO PERFORM ONE OR MORE ACTIONS 1212

FIG. 12

FAST PRESENCE DETECTION (FPD) OF A PERSON BASED ON A BREATHING WAVEFORM

RELATED APPLICATIONS

This application claims the benefit of U.S. Provisional Application No. 63/426,698, filed Nov. 18, 2022. The entire contents of which are incorporated by reference.

BACKGROUND

Monitoring devices can be used to track a user's activity. Some monitoring devices track a user's breathing activity and patterns while the user sleeps. Respiratory activity tracking can be used to identify sleep patterns (e.g., generate sleep scores and hypnograms) and monitor issues relating to cardiovascular or respiratory diseases or conditions. The monitoring device is typically positioned next to the user's bed (e.g., on a nightstand adjacent to the bed) and uses radar to detect movement within a detection zone to identify a respiratory waveform of a user. Monitoring devices can use radar sensors to detect the range, velocity, and identity of objects in motion. Radar sensors were originally designed for military and flight applications, but have more recently been manufactured as systems-on-a-chip in smaller form factors, making them adaptable for a wider range of commercial applications.

BRIEF DESCRIPTION OF DRAWINGS

The present invention will be understood more fully from the detailed description given below and from the accompanying drawings of various embodiments of the present invention, which, however, should not be taken to limit the present invention to the specific embodiments, but are for explanation and understanding only.

FIG. 3 is a flow diagram of a high-level data flow for sleep monitoring and FBD processing on a computing system according to at least one embodiment.

FIG. 12 is a flow diagram of a method for detecting an event representing a user entering a first region according to at least one embodiment.

DETAILED DESCRIPTION

Figure 1:
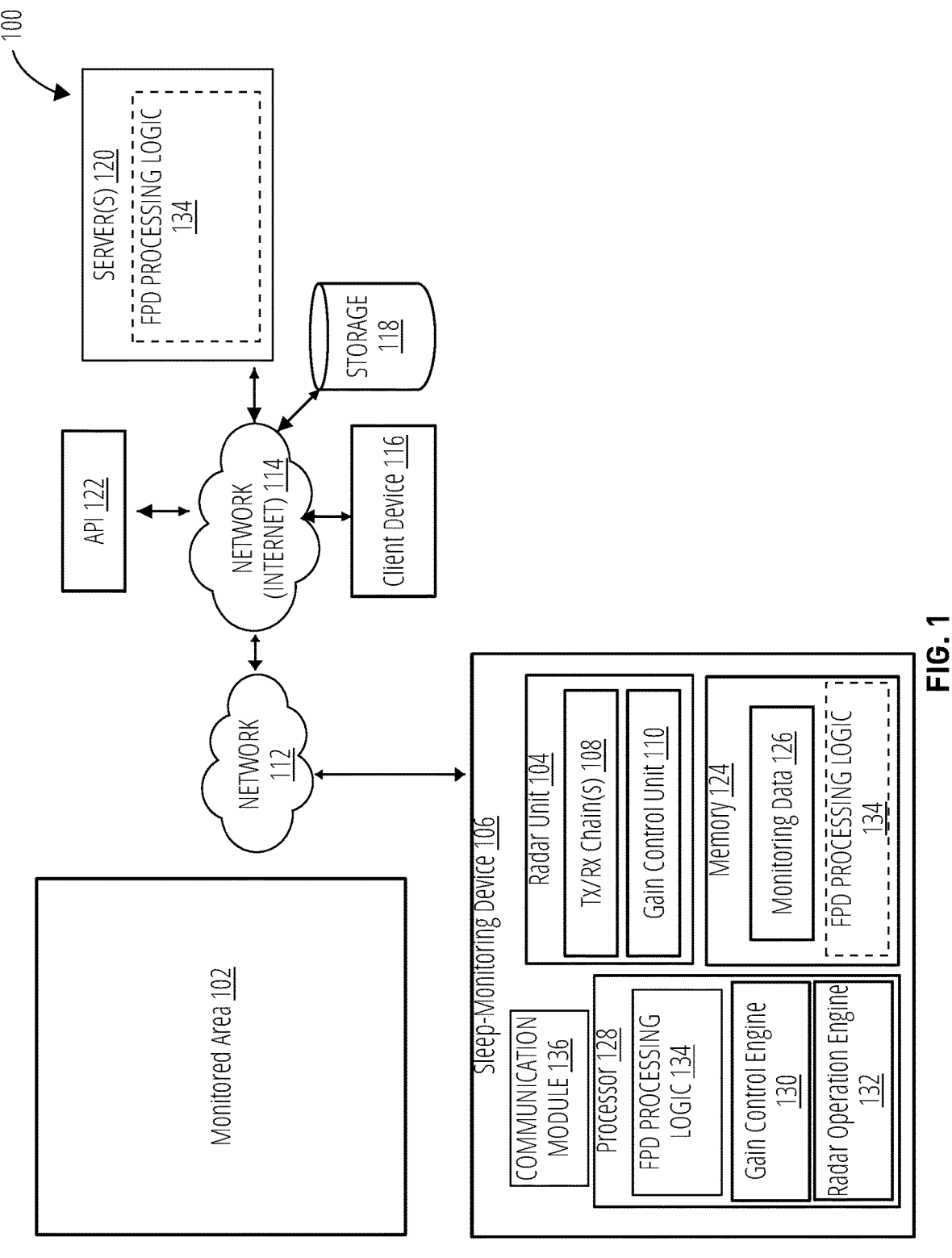
FIG. 1 depicts a device-based FPD system for smart routines including a sleep-monitoring device with a radar unit and FPD processing logic according to at least one embodiment.

Technologies of a device-based Fast Presence Detection (FPD) for a contactless sleep-monitoring device are described. A contactless sleep-monitoring device can use 60 GHz radar technology to monitor a person's breathing. Breathing data can be input into a machine learning (ML) model to predict different sleep stages based on the breathing data. Specifically, the sleep-monitoring device selects a body voxel to generate the ideal sleeping respiration waveform for ML-based sleep stage classification. When incorporating "Smart Routines," such as "sleep routines," to be triggered by data collected by the contactless sleep-tracking device, there is a challenge of quickly detecting that a user is getting into bed or getting out of bed. These routines depend on certain conditions or triggers (e.g., "Fell Asleep," "In bed," or "Out of bed) defined by a user. In a typical routine, one or more actions are executed as soon as the conditions or triggers are met. Conventionally, radar units do not output any metric that directly indicates motion based on energy. Even if the radar units can output activity level signals for energy-based detection, the location of the energy source is not available. Thus, some activity level signals would lead to false cases, such as a user entering the bedroom for non-sleep-related activity, which should not trigger a sleep routine.

Aspects and embodiments of the present disclosure address the above and other deficiencies by providing a Fast Presence Detection (FPD) processing logic that can detect an event of a user entering a bed or exiting a bed based on a breathing waveform (strongest breathing voxel information), range information, and confidence information collected by a contactless sleep-monitoring device. Event detection can be used to initiate one or more associated routines. Aspects and embodiments of the present disclosure can provide contactless sleep monitoring of an intended user sleeping closer to the sleep-monitoring device up to 1.5 meters (m) and without calibration.

Radar, also referred to as radio detection and ranging, is a detection system that uses radio waves to determine a distance (ranging), an angle, and/or a velocity of one or more objects. A radar unit includes a transmitter that produces electromagnetic waves in the radio or microwave domain and one or more receivers to measure electromagnetic waves reflected off an object. A radar unit can also be referred to as a radar sensor or a radar device. Although sometimes referred to as a radar sensor, it should be noted that a radar sensor has both a transmitter and one or more receivers to transmit a radar signal (radio waves) and receive or measure the reflected signals (reflected waves) from the radar signal encountering an object. The radio waves (pulsed or continuous) from the transmitter and reflected off the object given information about the object's location and speed. Aspects of the present disclosure can also be used with other sensing systems, such as an ultrasound unit. A sensing system can include at least one transmitter to transmit sound or electromagnetic waves and at least one receiver to measure reflected waves to determine a distance value between the sensing system and an object and an angle value between the sensing system and the object. Radar, as used herein, may be leveraged to measure human vital signs such as heart rate and respiratory rate such as to track sleep patterns to determine the quality of sleep metrics.

In at least one embodiment, an electronic device includes a radar unit that operates in a millimeter-wave (mmWave) frequency range. The electronic device may include a processing device coupled to the radar unit. The electronic device may include a memory coupled to the processing device to store data generated by the radar unit. The memory may further store computer-executable instructions that, if executed, cause the electronic device to perform operations. One method includes receiving radar data from a sleep-monitoring device with a radar unit. The radar data includes i) first data representing a breathing waveform associated with a user, ii) a first set of range values, and iii) a first set of confidence values associated with the first data. The method determines absolute magnitude values of the breathing waveform, first infinite impulse response (IIR) values using the first set of range values, and second IIR values using the first set of confidence values. The method determines a first event representing the user entering the first region using the absolute magnitude values and the first and second IIR values. The method sends a command to one or more devices in the environment that causes the one or more devices to perform one or more actions. The radar data may be associated with monitoring an environment of the monitoring device. For example, the monitored environment may include a sleeping environment, as illustrated and described below with respect to FIG. 1.

FIG. 1 depicts a device-based FPD system for smart routines 100 including a sleep-monitoring device 106 with a radar unit 104 and FPD processing logic 134 according to at least one embodiment. The sleep-monitoring device 106 may include a communication module 136 (e.g., a Wi-Fi communication chip), a processor 128, a radar unit 104, and a memory 124. The sleep-monitoring device 106 may be configured to monitor a monitored area 102 (e.g., a sleeping environment such as an environment including a bed). The processor 128 may include, and may also be referred to as, a controller or a microcontroller. The processor 128 may include multiple processors in some embodiments. The processor 128 can implement the FPD processing logic 134.

The sleep-monitoring device 106 may include a radar unit 104 that includes one or more transmission (Tx) chains and receiving (Rx) chains 108 to transmit and/or receive signals corresponding to respiratory-related motion occurring within a monitored area 102. The Tx/Rx chains 108 may include one or more millimeter-wave (mmWave) radar sensors to acquire radar data, such as detecting a breathing waveform (also referred to as a respiration waveform) of a person located within the monitored area 102. The radar unit 104 may further include a gain control unit 110. In an embodiment, the gain control unit 110 may include a fixed number of gain states. A gain state may include a representation of a gain value or, more generally, the gain of a transmitted radar signal. The gain of a radar antenna is a measure of the concentrated energy in the beam relative to the energy which would impinge upon a target if the same transmitted energy was emitted by an isotropic antenna. Each gain state adjusts a signal power associated with transmitting and/or receiving a radar signal. The gain state may be selected and updated according to a signal strength of the radar unit (e.g., dependent on the internal operating temperature).

According to an embodiment, the radar unit 104 includes one or more sensors (e.g., inertial measurement unit (IMU) sensors, magnetometer sensors, radar sensors, motion detectors, etc.) to collect and process data corresponding to monitored area 102, such as to monitor the respiratory activity of a user. For example, the radar unit 104 may be configured to detect the motion of a user. Motion data may be leveraged to initiate one or more procedures associated with gain control engine 130, and/or radar operation engine 132.

As shown in FIG. 1, the sleep-monitoring device 106 includes a processor 128. The processor 128 can execute the instructions stored in memory 140 to perform the operations described herein. The instructions can be computer-executable instructions that, if executed, cause the processor 128 (or sleep-monitoring device 106) to perform operations as described herein. As shown in FIG. 1, the processor 128 includes a gain control engine 130, and a radar operation engine 132. The various engine may be leveraged and coordinated by the processor 128 to carry out the methodology described herein. Though the processor 128 is described as having multiple processing engines, the division of functionality of the processor between each of the processing engines is purely exemplary.

The gain control engine 130 directs the radar unit 104 to perform gain control calibration. Gain control calibration may include sweeping the gain control unit 110 through various gain states and mapping a resulting signal power level associated with using each gain state. A gain state may be determined based on determining signal power levels corresponding to each gain state. In an embodiment, the gain state is determined by turning on the internal transmitter embedded in the Rx chain (separate from the Tx chain, not connected to any antenna) and measuring the power using the Rx chain. The feedback power is then converted to Effective Isotropic Radiated Power (EIRP) (e.g., based on calibration for each radar chip during production).

The radar operation engine 132 configured the radar unit 104 to transmit and acquire radar data. For example, the radar operation engine 132 may leverage Tx/Rx chains to acquire radar data, such as detecting a breathing waveform of a person located within the monitored area 102.

In an embodiment, the breathing waveform can be detected according to a suitable waveform extraction algorithm (e.g., a Doppler radar for noncontact vitals monitoring methodology). For example, the waveform extraction algorithm can include a multistage processing of radar outputs raw In-phase and Quadrature (I/Q) data of received echo signals. In an embodiment, the one or more radar sensors are used to "bin" the receive signals such that the receive signals are stored in a set of bins by the time of arrival relative to a transmit pulse. In an embodiment, the radar operation engine 132 checks the receive signal strength in the respective bins to enable the sorting of the returns across the different bins, which correspond to different ranges.

In an embodiment, a fast Fourier Transform (FFT) is implemented over these samples (a fast-time domain) to identify a channel response for each distance bin. In this example, another FFT is implemented over the frames within the respiration window (slow-time domain) for a set of candidate bins to determine which bin contains the respiration signal. In an embodiment, the bin corresponding to the desired respiration signal is selected based on a metric for periodicity and phase of that bin along the time domain to identify a selected or target waveform to be extracted.

In an embodiment, the one or more sensors of the radar unit measure a displacement of a user's chest to identify a respiratory rate associated with the user. In an embodiment, radar operation engine 132 uses three-dimensional imaging to generate a set of energy voxels corresponding to chest displacement movements and periodicity corresponding to a breathing pattern of the user. In an embodiment, the set of energy voxels is processed by the respiratory activity tracker to generate the respiration or breathing waveform corresponding to the user during a given sleep session.

In an embodiment, the processor 128 can generate a breathing waveform representing a respiratory rate or number of breaths a user takes per minute, referred to as respirations per minute (RPM) values. In an embodiment, the respiratory rate data and associated waveform can be further processed to generate one or more analytics indicative of a quality of sleep of the primary user. For example, the breathing waveform can be analyzed to generate a sleep score (e.g., an indication or score indicative of a quality of sleep). In an embodiment, a sleep score can be determined in accordance with a suitable sleep score generation methodology as a function of one or more factors, including an overall sleep time, a duration of the rapid eye movement (REM) sleep stage, a duration of a light sleep stage, a duration of a deep sleep stage, etc. In an embodiment, the sleep stages can be estimated using a machine learning (ML) model (e.g., a deep neural network) that takes the breathing waveform as the input. As described herein the sleep-monitoring device 106 can stream the radar data to the server(s) 120 for primary user identification (PUI) processing, estimating sleep stages, and sleep scores. As described herein, the FPD processing logic 134 can process the radar data for detecting an event of a user entering a first region (entering a bed) or exiting the first region (exiting a bed) to initiate one or more associated routines.

The memory 124 may be transitory and/or non-transitory and may represent one or both of volatile memory (e.g., static random access memory (SRAM), dynamic random access memory (DRAM), computational RAM, other volatile memory, or any combination thereof) and non-volatile memory (e.g., FLASH, read-only memory (ROM), magnetic media, optical media, other non-volatile memory, or any combination thereof). Part or all of the memory 140 may be integrated with the processor 128. The memory 124 can store monitoring data 126 (e.g., motion data (e.g., radar data), respiration rate data, and/or sleep quality) measured in the monitored area 102. The memory 124 can store instructions corresponding to a gain control engine 130, a radar operation engine 132, and the FPD processing logic 134.

In an embodiment, one or more radar sensors of the sleep-monitoring device 106 perform a localization of reflected signal in the 3D geometry, which is further subdivided into voxels. A voxel is a discrete volume element of graphic information in a three-dimensional (3D) space. The voxel can be used in the radar domain to represent the smallest volume element governed by a combination of range and angular resolution (e.g., also referred to as a range bin, angular bin individually in a 2D space). Each voxel carries information derived from a phase and amplitude of a reflected signal from corresponding geometric volume in the real world.

In an example mode of operation, the sleep-monitoring device 106 communicates with a wireless network 112 of a user. Although the wireless network 112 is referred to herein as "wireless," in some embodiments may not be wireless, such as where the sleep-monitoring device 106 is connected to the user's network via an Ethernet connection, for example. The wireless network 112 is connected to another network 114. The networks 112 and 114 may be the same network in some of the present embodiments. The networks 112 and 114, may include but are not limited to the Internet, a Wi-Fi® network compatible with the IEEE 802.11 standard and/or other wireless communication standard(s) including but not limited to WAP (Wireless Application Protocol), GPRS (General Packet Radio Service), GSM (Global System for Mobile Communication), LTE, VoLTE, LoRaWAN, LPWAN, RPMA, LTE Cat-"X" (e.g., LTE Cat 1, LTE Cat 0, LTE CatM1, LTE Cat NB1), CDMA (Code Division Multiple Access), TDMA (Time Division Multiple Access), FDMA (Frequency Division Multiple Access), and/or OFDMA (Orthogonal Frequency Division Multiple Access) cellular phone networks, Global Positioning System (GPS), CDPD (cellular digital packet data), Z-Wave, RIM (Research in Motion, Limited) duplex paging network, Bluetooth radio, an IEEE 802.11-based radio frequency network, or a combination thereof.

As described below, the sleep-monitoring device 106 may communicate with a client device 116 of the user via the wireless network 112 and/or the network 114. The client device 116 may include, for example, a computer, a laptop, a tablet, a mobile telephone (may also be referred to as a cellular telephone), such as a smartphone, a personal digital assistant (PDA), or another communication device capable of receiving and/or transmitting data across one or both of the networks 112 and 114. The client device 116 may include a display and related components capable of displaying data associated with the sleep-monitoring device 106. The client device 116 may also include a speaker and related components capable of providing alerts to the user or another person responsible for the user, and may also include a microphone. In some embodiments, one or more of the network 114, one or more server(s) 120, one or more remote storage device(s) 118, Application Programming Interface (API) 122, and client device 116 are associated with a cloud service. For example, one or more functions of the sleep-monitoring device 106 may be performed by the cloud service using one or more of network 114, server(s) 120, remote storage device(s) 118, API 122, and client device 116.

The sleep-monitoring device 106 may also communicate with one or more remote storage device(s) 118, server(s) 120, and/or API 122 via the wireless network 112 and the network 114 (Internet/PSTN). While FIG. 1 illustrates the remote storage device(s) 118, server(s) 120, and API 122 as components separate from the network 114, it is to be understood that the remote storage device(s) 118, server(s) 120, and API 122 may be considered to be components of the network 114.

In response to the detection of certain conditions by the sleep-monitoring device 106, the sleep-monitoring device 106 sends an alert to the client device 116 via the wireless network 112 and/or the network 114. The sleep-monitoring device 106 may also send motion data and/or respiration data (e.g., breathing waveform) to the client device 116 of the user (e.g., via the network 114 and/or the server(s) 120).

The motion data (e.g., radar data), respiration rate data, and/or sleep quality data captured by the radar unit 104 may be uploaded and recorded on the remote storage device(s) 118. In some of the present embodiments, the motion data, respiration rate data, and/or sleep quality data may be recorded on the remote storage device(s) 118, even if the user (or administrator) chooses to ignore the alert sent to the user's client device 116. In such embodiments, the user (or administrator) may access the motion data (e.g., radar data), respiration rate data, and/or sleep quality at a later time by accessing the remote storage device(s) 118 using the user's client device 116.

The API 122 may include, for example, a server (e.g., a bare-metal server, a virtual machine, or a machine running in a backend infrastructure as a service), or multiple servers networked together, exposing at least one API to the client(s) accessing it. These servers may include components such as application servers (e.g., software servers), depending upon what other components are included, such as a caching layer, database layers, or other components. The API 122 may, for example, include many such applications, each of which communicates with one another using their public APIs. In some embodiments, the API 122 may hold the bulk of the user data and offer the user management capabilities, leaving the clients with a very limited state.

The API 122 is a set of routines, protocols, and tools for building software and applications. An API expresses a software component in terms of its operations, inputs, outputs, and underlying types, defining functionalities that are independent of their respective implementations, which allows definitions and implementations to vary without compromising the interface. Advantageously, an API may provide a programmer with access to an application's functionality without the programmer needing to modify the application itself or even understand how the application works. An API may be for a web-based system, an operating system, or a database system, and it provides facilities to develop applications for that system using a given programming language. In addition to accessing databases or computer hardware like hard disk drives or video cards, an API can ease the work of programming graphical user interface (GUI) components. For example, an API can facilitate the integration of new features into existing applications (a so-called "plug-in API"). An API can also assist otherwise distinct applications with sharing data, which can help to integrate and enhance the functionalities of the applications. In at least one embodiment, the APIs can include routine APIs or a voice-assistant service API.

In various embodiments, the API 122 includes one or more services (also referred to as network services). A network service is an application that provides data storage, manipulation, presentation, communication, and/or other capabilities. Network services are often implemented using a client-server architecture based on application-layer network protocols. Each service may be provided by a server component running on one or more computers (such as a dedicated server computer offering multiple services) and accessed via a network by client components running on other devices. However, the client and server components can both be run on the same machine. Clients and servers may have a user interface and sometimes other associated hardware.

Figure 2:
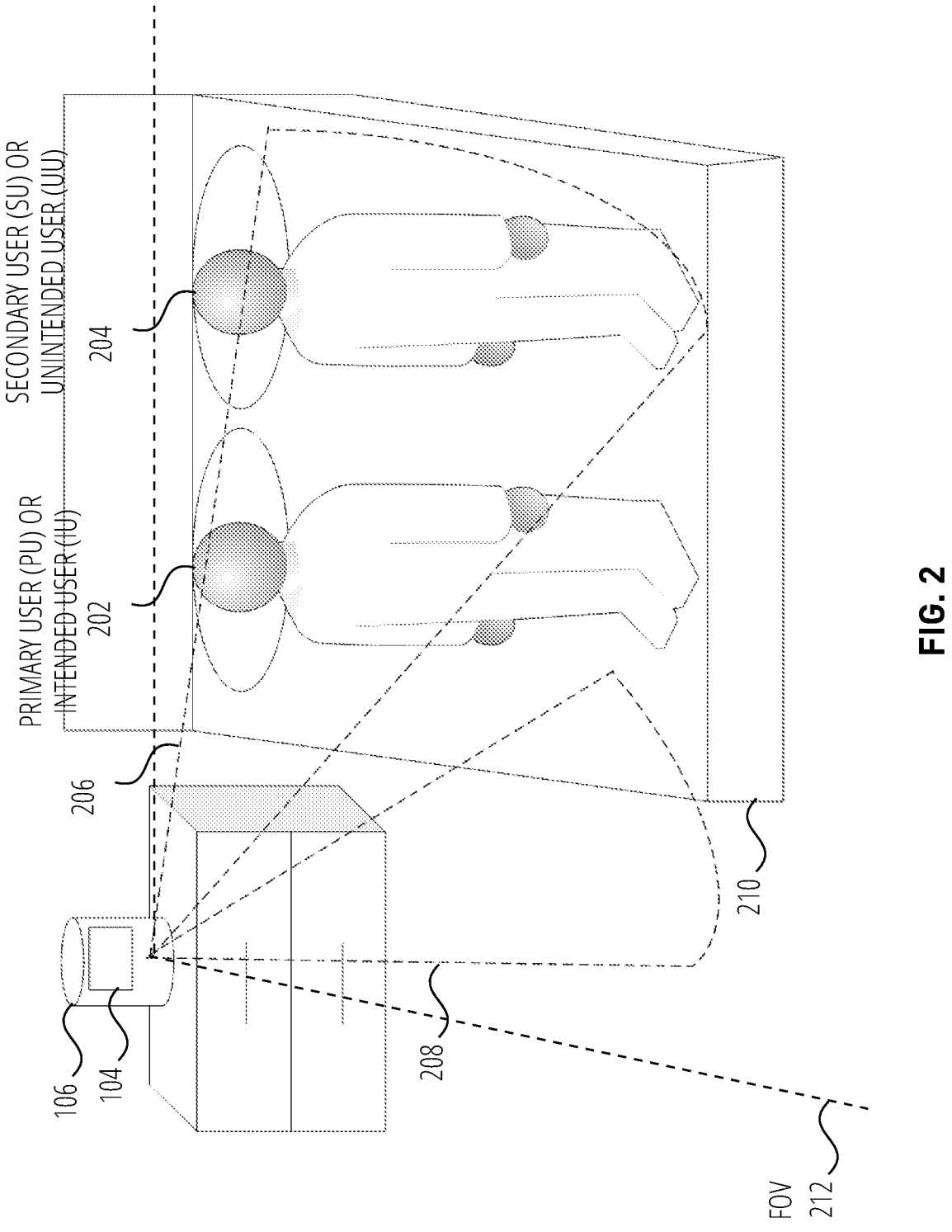
FIG. 2 illustrates a monitored area adjacent to the sleep-monitoring device of FIG. 1, according to at least one embodiment.

In at least one embodiment, the sleep-monitoring device 106 can monitor human activity within a field of view (FOV) 212 of the radar unit 104, as illustrated in FIG. 2.

FIG. 2 illustrates a monitored area 102 adjacent to the sleep-monitoring device 106 of FIG. 1, according to at least one embodiment. The sleep-monitoring device 106 can generate radar data, including any combination of the following: i) first data representing a breathing waveform, ii) range values representing a physical distance between a body and the radar unit 104, iii) respirations per minute (RPM) values of the breathing waveform, iv) confidence values associated with the RPM values; v) second data representing an amount of motion of the body in a first region 206, vi) third data representing an amount of motion of the body in a second region 208. The first region 206 can correspond to a bed 210, located in an environment around the sleep-monitoring device 106. The second region 208 can be adjacent to the bed 210. The sleep-monitoring device 106 can generate a digital boundary representing the first region 206 within the field of view of the radar unit 104. The sleep-monitoring device 106 can generate a digital boundary representing the second region 208 within the field of view of the radar unit 104.

In at least one embodiment, the sleep-monitoring device 106 can detect, using the radar unit 104, the presence and/or motion of one or more users, including an intended user (IU) 202 (also referred to as primary user (PU) and an unintended user (UU) 204 (also referred to as secondary user (SU), within the digital boundary corresponding to the first region 206. The sleep-monitoring device 106 can detect, using the radar unit, the presence and/or motion of the one or more users within the digital boundary corresponding to the second region 208. The radar unit 104 can report, to the FPD processing logic 134, the presence and/or motion within the second region 208 as an out-of-bed (OOB) indicator. The radar unit 104 can report, to the FPD processing logic 134, the presence and/or motion within the second region 208 as IN/OUT activity. In the example illustrated in FIG. 2, IU 202 and UU 204 lie on the bed 210 and are within the FOV 212 of the radar unit 104 within the first region 206. Digital data generated by the radar unit, or "radar data" in short, may be used by the FPD processing logic 134 to identify one or more bodies in the first region 206 or second region 208 as IUs or UUs, as well as detect the events associated with entering and exiting the first region 206, as described in more detail below with respect to FIG. 3 to FIG. 14.

In at least one embodiment, the sleep-monitoring device 106 may be a smart-home IoT device, such as a voice-assistant device, that may connect to at least one access point device and/or a network (e.g., a wireless local area network (WLAN), a wide area network (WAN), or cellular). The sleep-monitoring device 106 may be located in a room (or other space) in a building in order to detect and identify users within the room (or other space). The sleep-monitoring device 106 can transmit wirelessly over multiple channels to one or more other devices (not illustrated in FIG. 1), such as an access point device. The access point device may be in the same or a different room than the sleep-monitoring device 106. In some embodiments, the sleep-monitoring device 106 can operate in frequency bands other than 2.4 GHZ, such as other industrial, scientific, and medical (ISM) bands like 5 GHZ, cellular frequency bands (e.g., 4G LTE, 5G), or the like. In at least one embodiment, the sleep-monitoring device 106 can collect radar data and send the radar data to the FPD processing logic 134. The FPD processing logic 134 can process the radar data to detect an event of a user entering or exiting an area of interest, as described in detail below. In various embodiments, the sleep-monitoring device 106 and FPD processing logic 134 may determine, using the radar data, whether a human presence has been detected in the first region to initiate one or more routines to be performed by one or more devices associated with the environment.

FIG. 3 is a flow diagram of a high-level data flow for sleep monitoring and FPD processing 300 on a computing system according to at least one embodiment. The sleep processing 300 can be implemented in a sleep processing service 318 hosted on a cloud computing system (not illustrated in FIG. 3). The sleep processing 300 contains an FPD algorithm (also referred to as FPD Processing logic) and read and write operations required for streaming mode operation. The sleep processing 300 begins with binary files being uploaded to a storage service from a sleep-monitoring device (not illustrated in FIG. 3) (block 302). For example, the sleep-monitoring device can upload the binary files into a cloud object storage (e.g., S3 bucket). The sleep processing 300 can access the binary files in the cloud object storage and pre-process the binary data. In at least one embodiment, the sleep processing 300 can convert the binary data to data frames (block 304). A data frame can contain radar data corresponding to a given period. For example, a first period can include a set of data frames (e.g., 400). The sleep processing 300 can process each frame at block 306 to determine a PUI and presence output states for the respective frame. The data frame data can also be processed in a separate FPD processing pipeline 320 to detect a user entering (or exiting) a first region (e.g., a user entering the bed) using the breathing waveform, range values, and confidence values, as described in more detail below. The FPD processing pipeline 320 can be used to detect other conditions using the breathing waveform, range values, and confidence values, as well as other features of the data, such as out-of-bed indicator (OOBI) information, RPM values, or the like. At block 308, the sleep processing 300 performs sleep data reconciliation. At block 308, the sleep processing 300 reconciles sleep stage predictions with PUI and presence output states determined at block 306. The sleep processing 300 can input the sleep data into a sleep monitoring service for sleep score computation and hypnogram generation (block 310).

At block 312, various operations are performed on a set of frames. Each data frame of the set of data frames can include i) one of the absolute magnitude values of the breathing waveform, ii) one of the first IIR values, and iii) one of the second IIR values. In other embodiments, the data frame can contain a magnitude value of the breathing waveform, a range value, and a confidence value, and the processing logic can compute an absolute magnitude value, an IIR value for a window of range values, and an IIR value for a window of confidence values. At block 312, the processing logic can determine a first count of data frames in the set of data frames having an absolute magnitude value that satisfies a first criterion. At block 312, the processing logic can determine a second count of data frames in the set of data frames having a first IIR value that satisfies a second criterion. At block 312, the processing logic can determine a third count of data frames in the set of data frames having a second IIR value that satisfies a third criterion. At block 314, the processing logic can determine a first event that represents the user entering the first region (e.g., bed) in response to the first count exceeding a first threshold, the second count exceeding a second threshold, and the third count exceeding a third threshold, such as described in more detail below with respect to FIG. 6.

In another embodiment, at block 312, the processing logic can determine a first count of data frames in the set of data frames having an absolute magnitude value that satisfies a first criterion. At block 312, the processing logic can determine a second count of data frames in the set of data frames having a first IIR value that satisfies a second criterion. At block 312, the processing logic can determine a third count of data frames in the set of data frames having a second IIR value that satisfies a third criterion. At block 312, the processing logic can determine a fourth count of data frames where the first count does not exceed a first threshold, the second count does not exceed a second threshold, or the third count does not exceed a third threshold. At block 314, the processing logic can determine the first event (e.g., user entering the bed) in response to the first count exceeding the first threshold, the second count exceeding the second threshold, the third count exceeding the third threshold, and the fourth count exceeding a fourth threshold, such as described in more detail below with respect to FIG. 7.

If the first event is detected at block 314, the processing logic can send one or more commands to initiate one or more routines. The routines can include one or more actions performed by one or more devices in the environment or associated with the environment. If the first event is not detected at block 314, the processing logic can return to block 314 to continue FPD processing.

In at least one embodiment, the processing logic can determine a current time of the first event at block 314. The processing logic can prevent the command from being sent at block 316 in response to the current time occurring before or after a time period. In at least one embodiment, the user can specify a period in which the routines can be triggered, such as a bedtime window of 10 pm-12 am. In at least one embodiment, the processing logic can only be enabled during the bedtime window.

In at least one embodiment, at block 306, the processing logic can save data frame input in a database (e.g., DynamoDB). The sleep processing 300 can perform frame-level processing for PUI state boundary and state transition predictions. The frame-level processing can be done with a processing chunk, including the radar data of the current data frame and some radar data of a previous data frame. For example, a 7-minute processing chunk can include a previous 2-minute chunk of radar data from a previous frame and a current 5-minute chunk of radar data. The sleep processing 300 can generate IU or UU annotations for the 5-minute chunk of radar data (i.e., the current frame) based on the frame-level predictions. The sleep processing 300 can generate timestamp annotations for the 5-minute chunk of radar data (i.e., the current frame). The sleep processing 300 can save the PUI results, presence outputs, and the last two-minutes of radar data of the current data frame into the PUI datastore and continue processing a next data frame. The last-two minutes of radar data are used with the next data frame.

In a further embodiment, the various frame-level operations performed on each frame can include some post-processing functions to handle duplicate OOBIs and any rewrites for IU→IU or IU→UU transitions. Once the session begins, IU is the default start state. However, the session could have been started by IU or UU. So, in order to handle the scenario of UU in bed before IU, the post-processing functions need to rewrite all the data marked as IU until the actual UI enters the bed. This leads to rewriting for older data to UU when IU followed by an IU scenario (IU→IU transition) is encountered.

In at least one embodiment, the sleep processing 300 is implemented on a computing device including one or more processors and memory to store computer-executable instructions that, if executed, cause the one or more processors to receive radar data from a sleep-monitoring device including a radar unit and generate a first set of data frames using the radar data. In at least one embodiment, the first set of data frames includes i) a first set of range values associated with a first period, each range value representing a physical distance between a body and the radar unit, ii) a first set of RPM values of a breathing waveform associated with the first period, iii) a first set of confidence values associated with the first set of RPM values, iv) first data representing an amount of motion of the body on a bed located in an environment around the sleep-monitoring device, and v) second data representing an amount of motion of the body in a region adjacent to the bed. The confidence values can represent an amount of confidence (e.g., percentage or value between 0 and 1) that the first set of RPM values represents human breathing.

In a further embodiment, the sleep processing 300 can generate a second set of data frames using the radar data corresponding to a second period after the first period. The sleep processing 300 can determine, using the second set of data frames, an event where the body entered or exited the region adjacent to the bed during the second period.

As described above, in dual-user scenarios, disambiguating between the breathing of an intended user (IU) sleeping closer to the radar unit from an unintended user (UU) sleeping farther from the radar unit is critical. The sleep score of only the IU should be determined by a device-based PUI algorithm. As described above, the PUI processing can disambiguate between IU and UU from the radar data by processing the radar data at a frame level using a PUI algorithm. The goal of the PUI algorithm is to distinguish between UU's sleep data from UI's sleep data and correctly capture the IU's sleep data to minimize the missing detection rate of incorrectly discarding the IU's sleep data. The PUI algorithm can detect transitions in the radar data using different types of transition logic. In at least one embodiment, the PUI algorithm can use a hybrid approach to detecting transitions in the radar data.

PUI Post Processing

Referring to FIG. 3, the sleep processing 300 performs post-processing functions at block 306. The post-processing functionality can be implemented in a post-processing module or post-processing logic that is added on top of the PUI predictions to handle different user scenarios where changes need to be made to the predicted output stored in the PUI data store (e.g., DynamoDB). These functions also introduce the time and memory aspect needed for making corrections to PUI predictions at a session level. Following are the three major functionalities of the PUT post-processing module: handling duplicate OOBIs and IU rewrite.

Handling Duplicate OOBIs

Two minutes of the previous chunk data is added while processing the current chunk. So, there is a possibility that the same OOBI (present in these two minutes) is qualified twice. In some cases, the state change decisions made in these two instances are different, although they have the same absolute timestamp (OOBI). This happens because the samples used for post- and pre-averaging data will differ. The decision made in the second instance is more accurate as it has better data for post- and pre-averaging. In these cases, the entries in the PUI data store (e.g., Dynamo DB) made by the first instance are deleted and updated as per the decisions made by the second instance.

IU→IU Rewrite

Once the session begins, IU is the default start state. However, the session could have been started by IU or UU. So, in order to handle the scenario of UU in bed before IU, the post-processing module needs to rewrite all the data marked as IU until the actual UI enters the bed. This leads to rewriting for older data to UU when IU followed by an IU scenario (IU→IU transition) is encountered.

Figure 4:
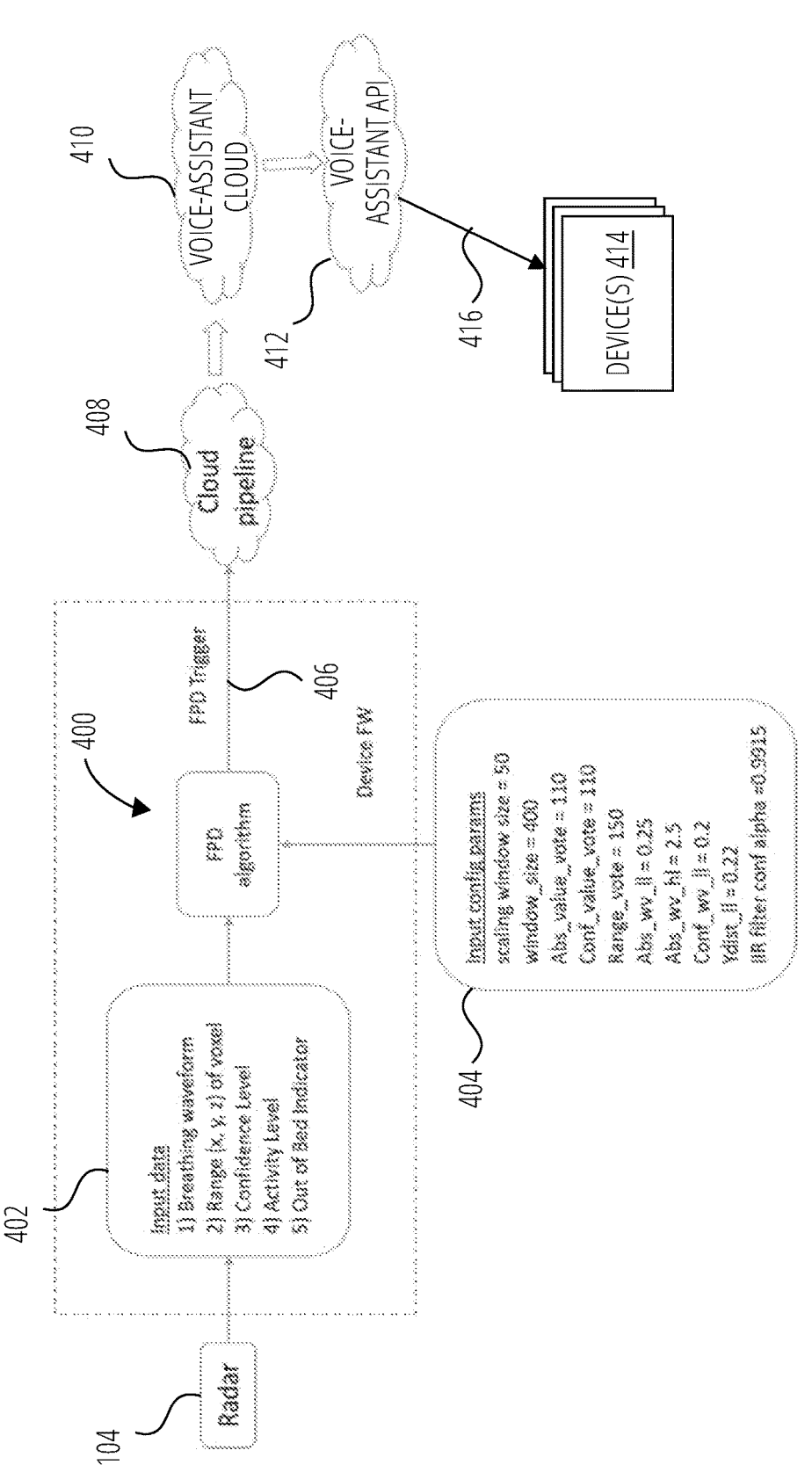
FIG. 4 is a block diagram of an FPD algorithm according to at least one embodiment.

FIG. 4 is a block diagram of an FPD algorithm 400 according to at least one embodiment. The FPD algorithm 400 can be implemented in hardware (e.g., circuitry, dedicated logic, programmable logic, microcode, processing device, etc.), software (such as instructions run on a processing device, a general-purpose computer system, or a dedicated machine), firmware, microcode, or a combination thereof. The FPD algorithm 400 may be implemented by the FPD processing logic 134. The FPD algorithm 400 may be implemented, for example, by the sleep-monitoring device 106 with the radar unit 104. The FPD algorithm 400 can initiate one or more "Smart Routines" without express user input. The routines can depend on triggers, i.e., "Fell Asleep," "In bed," or "Out of bed," which the users can choose. In a typical routine, the actions are executed as soon as the triggers are fired. As described above, in the context of sleep routines, there is a challenge in quickly detecting that a user is getting in bed. The FPD algorithm 400 can be used for this purpose. This FPD algorithm 400 can be used as an input to the "In-bed" trigger. It is important to note that the FPD algorithm 400 can service convenience routines, e.g., lights, music, or the like. The FPD algorithm 400 may not necessarily be used for strict routines (e.g., security use cases, starting cameras, or the like). The FPD algorithm 400 can be implemented in a separate pipeline in an end-to-end implementation. In at least one embodiment, a goal of the FPD algorithm 400 is to detect presence with a precision and recall rate of 92% and a latency of fewer than 65 seconds (e.g., TP90 latency <65 s). This can be used to generate an "In-Bed Trigger." The In-Bed trigger would be further used to map to routines (e.g., dim lights, play sleep sounds, turn off television). In at least one embodiment, the FPD algorithm 400 can use a period, such as a bedtime window (e.g., 10 pm-12 am). The user can input or select a time range for the bedtime window. The FPD algorithm 400 can prevent the FPD trigger from occurring outside this period. That is, the FPD algorithm 400 can ensure that only FPD triggers within this window are actionable.

The FPD algorithm 400 can receive radar input data 402 generated by the radar unit 104 of the sleep-monitoring device 106. The radar input data 402 can include the breathing waveform of a body voxel, the range (e.g., x, y, z coordinates) of the body voxel, a confidence level associated with the body voxel, an activity level of the body voxel, and out-of-bed indicator (OOBI) information. A 3D cartesian space around the radar unit 104 is divided into voxels (e.g., 10 cm×10 cm×10 cm). In simple terms, a body voxel or simply voxel is the 3D version of a pixel. The range of the body voxel is the distance (e.g., x, y, z distance) between the radar unit and the voxel. The FPD algorithm 400 can also receive input configuration parameters 404. The input configuration parameters 404 can include a scaling window size (e.g., 50), a window size (e.g., 400), a first threshold representing an absolute value voting threshold (e.g., 110), a second threshold representing (e.g., 110), a second threshold representing a range value voting threshold (e.g., 150), a third threshold representing a confidence value voting threshold (e.g., 110), a first value of a range (e.g., 0.25) and a second value of the range (e.g., 2.5), a minimum confidence threshold (e.g., 0.2), a minimum range threshold (e.g., 0.22), and an IIR filter confidence threshold (e.g., a single-pole low-pass IIR filter, such as with IIR filter conf alpha=0.9915). Using radar input data 402 and input configuration parameters 404, the FPD algorithm 400 can determine whether there is an FPD event 406 (e.g., FPD trigger). An indication of the FPD event 406 can be sent to a cloud pipeline 408 that manages routines. The cloud pipeline 408 can forward the FPD event 406 to a voice-assistant cloud service 410 (e.g., Alexa service developed by Amazon Technologies). The voice-assistant cloud service 410 can use a voice-assistant API 412 to send one or more command(s) 416 to one or more device(s) 414 to perform one or more actions.

In at least one embodiment, the one or more device(s) 414 can be a light, such as a smart lightbulb. The FPD event 406 can represent the user entering a bed in the first region. The one or more actions can include dimming the light, turning off the light, or changing a color of the light. In embodiments where the FPD event 406 represents the user exiting the bed, the one or more actions could include turning on the light.

In at least one embodiment, the one or more device(s) 414 can be a speaker. The FPD event 406 can represent the user entering a bed in the first region. The one or more actions can include playing a sleep sound using the speaker, playing a song using the speaker, or turning off the speaker.

In at least one embodiment, the FPD event 406 represents the user entering a bed in the first region. One or more actions can include locking a door, activating an alarm system, turning on a television, or turning off a television. The actions can be performed on one or more devices, such as a group of devices, or a scene including one or more devices.

Figure 5:
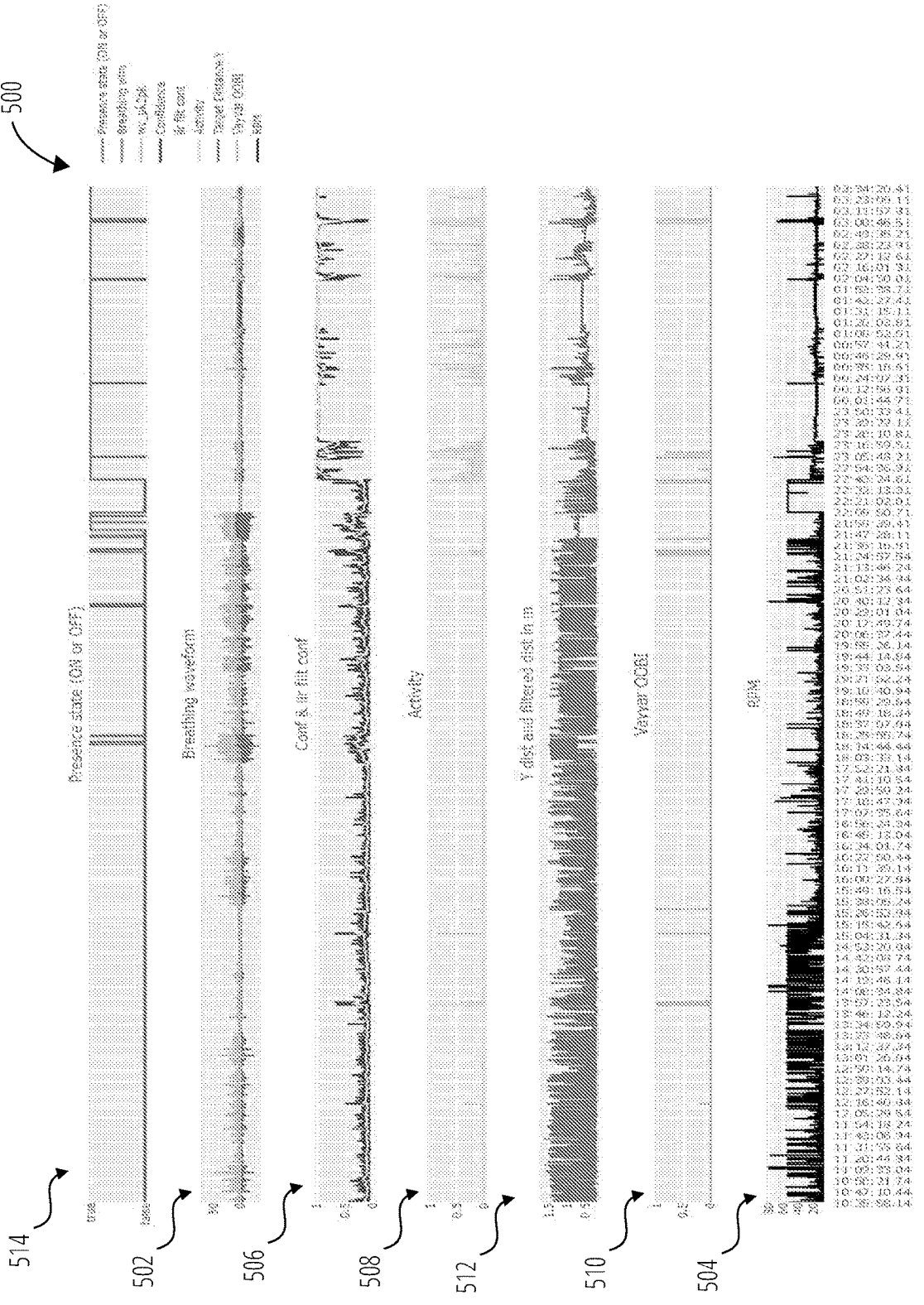
FIG. 5 is a graph of radar data and a presence state for a primary sleep session according to at least one embodiment.

In at least one embodiment, radar input data 402 can be generated by the radar unit 104. The radar unit 104 can generate a breathing waveform after locking onto a voxel with the highest score. In addition, there are different metrics available from the digital signal processor (DSP) of the radar unit 104, such as the range of a voxel (x, y and z), confidence level, activity, Out-of-bed Indicator and respirations per minute (RPMs) of the breathing waveform, such as illustrated in FIG. 5. It should be noted that the radar unit 104 can output the breathing waveform (and its corresponding characteristics) to be used as the primary metric to detect the presence of the user entering the bed. The breathing waveform can be used as a direct indicator of the presence of a human. Since presence has to be detected within 65 seconds of the person being present in the bed, the FPD algorithm 400 can have a simple algorithm design. In this primary metric, the goal is to separate direct current (DC) (baseline) versus the presence of some breathing signal. Multiple post-processed metrics can be used, such as waveform peak-to-peak values, absolute values of the breathing waveform, power of the breathing waveform, and RPMs of the breathing waveform. In at least one embodiment, the absolute values of the breathing waveform can be the simplest to implement and can separate DC from the presence of a breathing signal.

Even separating the DC from the presence of a breathing signal is a strong indicator, it may not be enough to qualify the presence. For example, a periodic signal within 4-40 RPM may not be filtered out by the radar unit's DSP and can be misinterpreted as presence, as shown in FIG. 5. The additional metric, called confidence level or confidence values, can be used to separate noise from actual breathing waveform. Even after filtering based on confidence level, there may be some cases where the confidence level is high for a noisy waveform. The radar unit can lock onto a noisy voxel very close to the radar unit in the absence of any high-scoring target voxel. In this case, the radar unit could start tracking voxels from a range of 0.2 m to 1.7 m. The range information can help qualify the presence. For example, if a voxel of 0.21 m or lower is continuously tracked, this can be safely ignored as a noisy voxel.

FIG. 5 is a graph 500 of radar data and a presence state for a primary sleep session according to at least one embodiment. The radar data can include i) first information 502 representing a breathing waveform. The breathing waveform can have magnitude values, and the breathing waveform can be used to generate absolute magnitude values of the breathing waveform, as illustrated in the two signals of the first information 502. The radar data can include ii) second information 504 representing RPM values associated with the body. The radar data can include iii) third information 506 representing confidence values associated with the RPM values. The third information 506 can include the confidence values and the first infinite impulse response (IIR) values of the confidence values. The radar data can include iv) fourth information 508 representing motion levels (activity levels) of the body in a first region 206 of the environment. The radar data can include v) fifth information 510 representing motion in a second region 208 adjacent to the first region 206. In at least one embodiment, the fifth information 510 includes spikes in a sixth row of the graph 500, each spike representing an OOBI (or an IN/OUT event). The OOBI signal can range between 0 and 1 to quantify an activity level observed in the second region 208 (e.g., an out-of-bed region) during a given time. The radar data can include vi) sixth information 512 representing range values of a body located in an environment around the sleep-monitoring device. The sixth information 512 can include the range values and the second IIR values of the range values.

The third information 506, in a third row of the graph 500, shows the confidence of the selected body voxel's breathing waveform. The fourth information 508 indicates the motion level of the in-bed activity level (e.g., in the first region 206). Both of these signals can range from 0 to 1. As illustrated in FIG. 5, the sixth information 512 and second information 504 denote the range distance of the selected body voxel and the estimated RPM of the respiration rate. The sleep processing 300 uses the radar data (e.g., data metrics) described above to detect a presence state 514 of the user in the first region, such as a user entering the bed. The presence state 514 results from the sleep processing 300 determining the user's presence using the FPD processing pipeline 320, as described above.

As illustrated in FIG. 5, there are some spikes in the presence state 514 that can be detected but ignored until certain criteria are met, as described below with respect to FIG. 6 and FIG. 7. For example, presence threshold qualifications can be derived from distributions of these metrics in a controlled environment. These presence threshold qualifications can be modified once deployed. The presence threshold qualifications can be part of ground truth data that is used for quickly detecting the user's presence in the first region. In some cases, a minimum absolute value threshold (abs_wv_ll) can be used without a maximum absolute value threshold (abs_wv_hl) to avoid missing a presence of a higher amplitude waveform.

Figure 8:
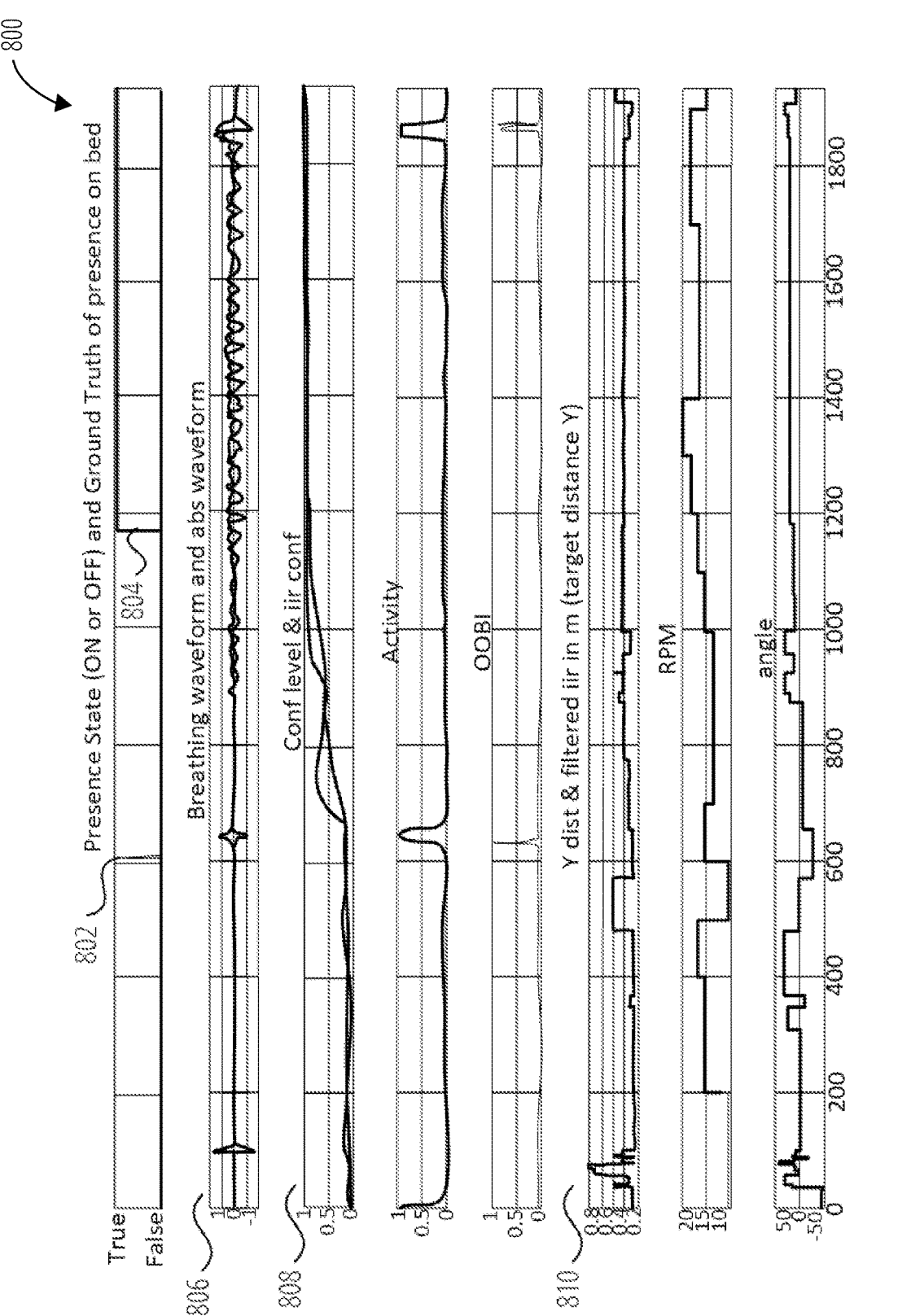
FIG. 8 is a graph illustrating FPD detection with respect to ground truth data according to at least one embodiment.

In at least one embodiment, the FPD algorithm 400 uses the breathing waveform, IIR-filtered confidence levels, and IIR-filtered range values to determine a user's presence in the first region. A moving window of a set of frames (e.g., 400 frames) can be used to validate if each of the metrics individually meets a certain criterion per frame. This moving window can be backward-looking, and hence a first output of the FPD algorithm 400 is produced at the Nth frame (e.g., 400th frame). When using the ground truth data, the detection delay is calculated with respect to the ground truth data and not the start of the dataset. The delay can be smaller than 40 seconds, as shown in FIG. 8.

As described with respect to FIG. 4, the high-level block diagram shows how the FPD algorithm 400 can be used to generate an "In-bed" trigger. Described below with respect to FIG. 6 and FIG. 7, are two detailed flow charts describing different embodiments of the processing by the 400.

Figure 6:
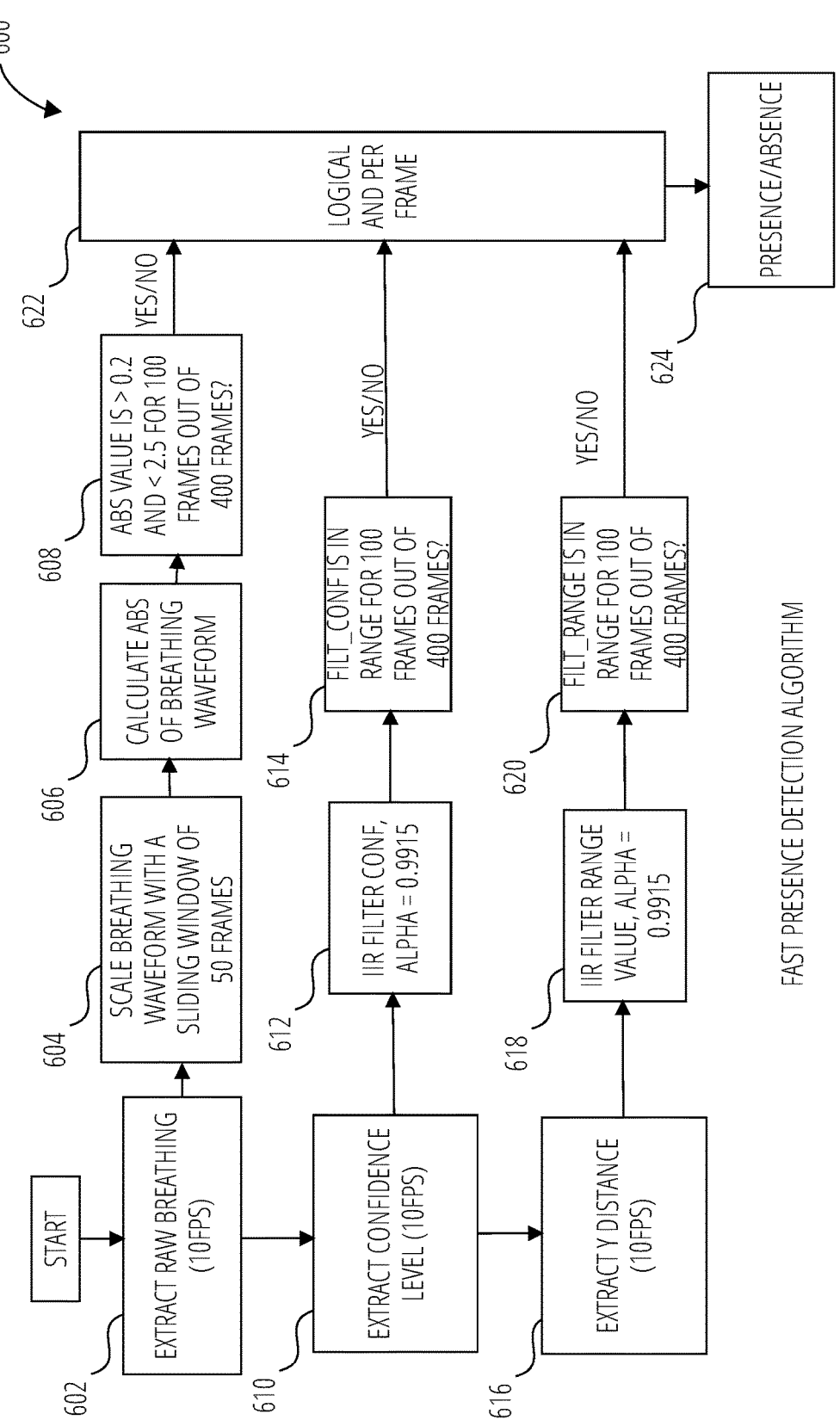
FIG. 6 is a flow diagram of an FPD process according to at least one embodiment.

FIG. 6 is a flow diagram of an FPD process 600 according to at least one embodiment. The FPD process 600 may be performed, at least in part, by processing logic that may include hardware (e.g., circuitry, dedicated logic, programmable logic, microcode, processing device, etc.), software (such as instructions run on a processing device, a general-purpose computer system, or a dedicated machine), firmware, microcode, or a combination thereof. The FPD process 600 may be implemented, for example, by the sleep-monitoring device 106. The FPD process 600 may be implemented, for example, by a computing device with the FPD processing logic 134. The FPD process 600 may be implemented, for example, by one or more server(s) 120 hosting the FPD processing logic 134 in connection with the sleep-monitoring device 106 with the radar unit 104.

Figure 9:
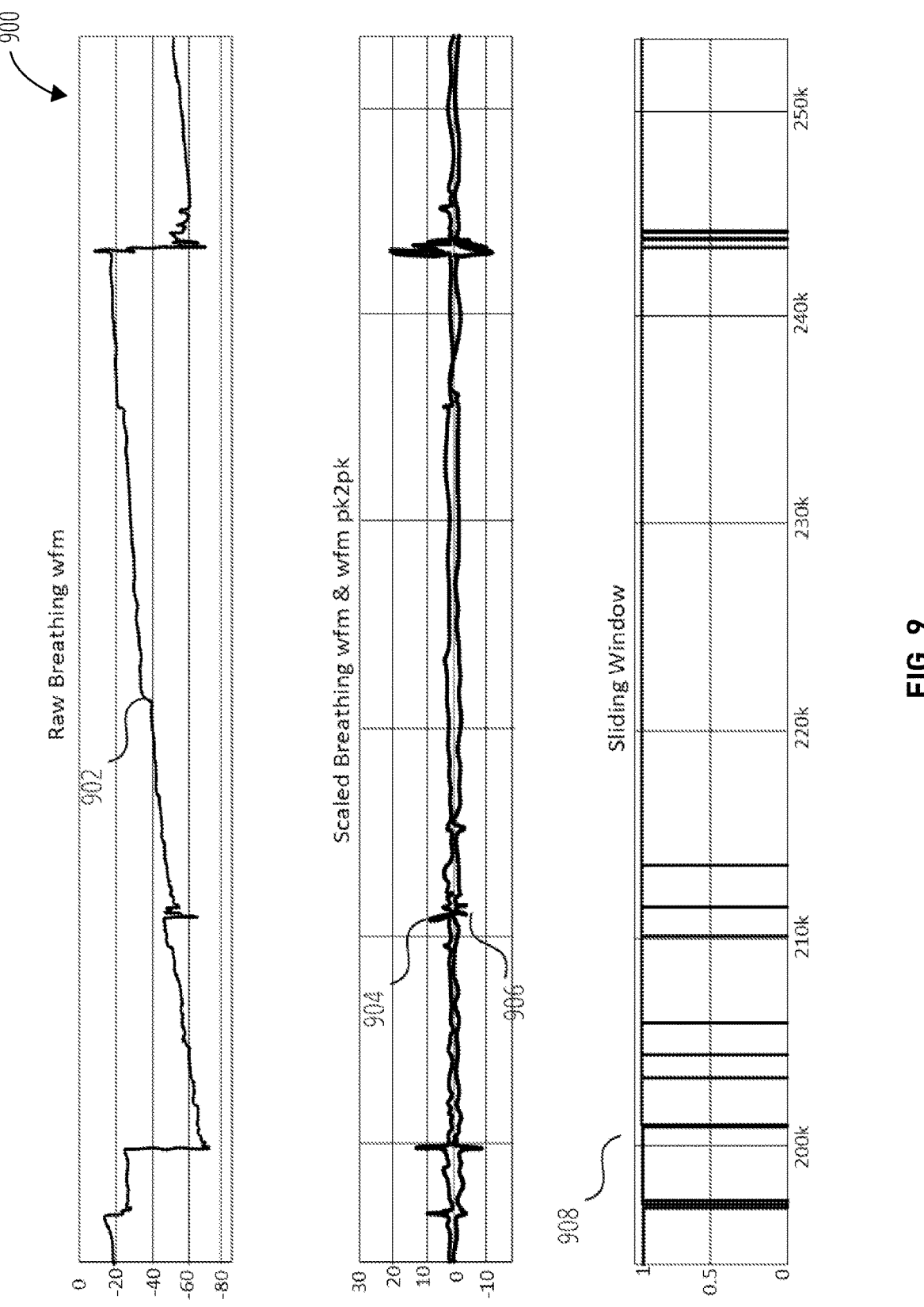
FIG. 9 is a graph illustrating the scaling of breathing waveform according to at least one embodiment.

The FPD process 600 begins with the processing logic extracting raw breathing samples of the breathing waveform from the radar data (block 602). The radar data can include a set of data frames, each data frame of the set of the data frames comprises i) raw breathing data, ii) a range value, and iii) a confidence value. The breathing waveform can be sampled at a sampling rate (e.g., 10 frames per second). The processing logic can scale the breathing waveform with a sliding window of a set number of frames (e.g., 50 frames) (block 604). In some embodiments, the breathing waveform needs to be scaled because it has a moving DC offset, as shown in FIG. 9. The processing logic can calculate the absolute magnitude values of the breathing waveform (block 606). The processing logic can determine if a first count of data frames in the set of data frames (e.g., 400) has an absolute magnitude value that satisfies a first criterion (block 608). In at least one embodiment, the first criterion is that the first count exceeds a first threshold (e.g., 110 of 400) of a number of frames having an absolute magnitude value in a specified range, defined by a minimum threshold and a maximum threshold (e.g., abs value is >0.2 and <2.5).

At block 610, the processing logic extracts the confidence values from the radar data. The processing logic can determine an IIR confidence value (block 612) (e.g., alpha=0.9915). The confidence values can be sampled at a sampling rate (e.g., 10 frames per second). The processing logic determines a second count of data frames in the set of data frames having an IIR confidence value that satisfies a second criterion (block 614). In at least one embodiment, the second criterion is that the second count exceeds a second threshold (e.g., 110 of 400) of a number of frames having an IIR confidence value in a specified range, defined at least by a minimum threshold (e.g., conf_wv_ll=0.2).

At block 616, the processing logic extracts the range values (y distance) values from the radar data. The range values can be sampled at a sampling rate (e.g., 10 frames per second). The processing logic can determine an IIR range value (block 618) (e.g., alpha=0.9915). The processing logic determines a third count of data frames in the set of data frames having an IIR range value that satisfies a third criterion (block 620). In at least one embodiment, the third criterion is that the third count exceeds a second threshold (e.g., 150 of 400) of a number of frames having an IIR range value in a specified range, defined at least by a minimum threshold (e.g., Ydist_ll=0.22).

At block 622, the processing logic can determine an event representing the user entering the first region (presence/absence) in response to the first count exceeding the first threshold at block 608, the second count exceeding the second threshold at block 614, and the third count exceeding the third threshold at block 620. The processing logic can make this determination on a frame basis. When the event is detected, the processing logic outputs a presence signal or an indication of the event or an absence signal (block 624).

Figure 7:
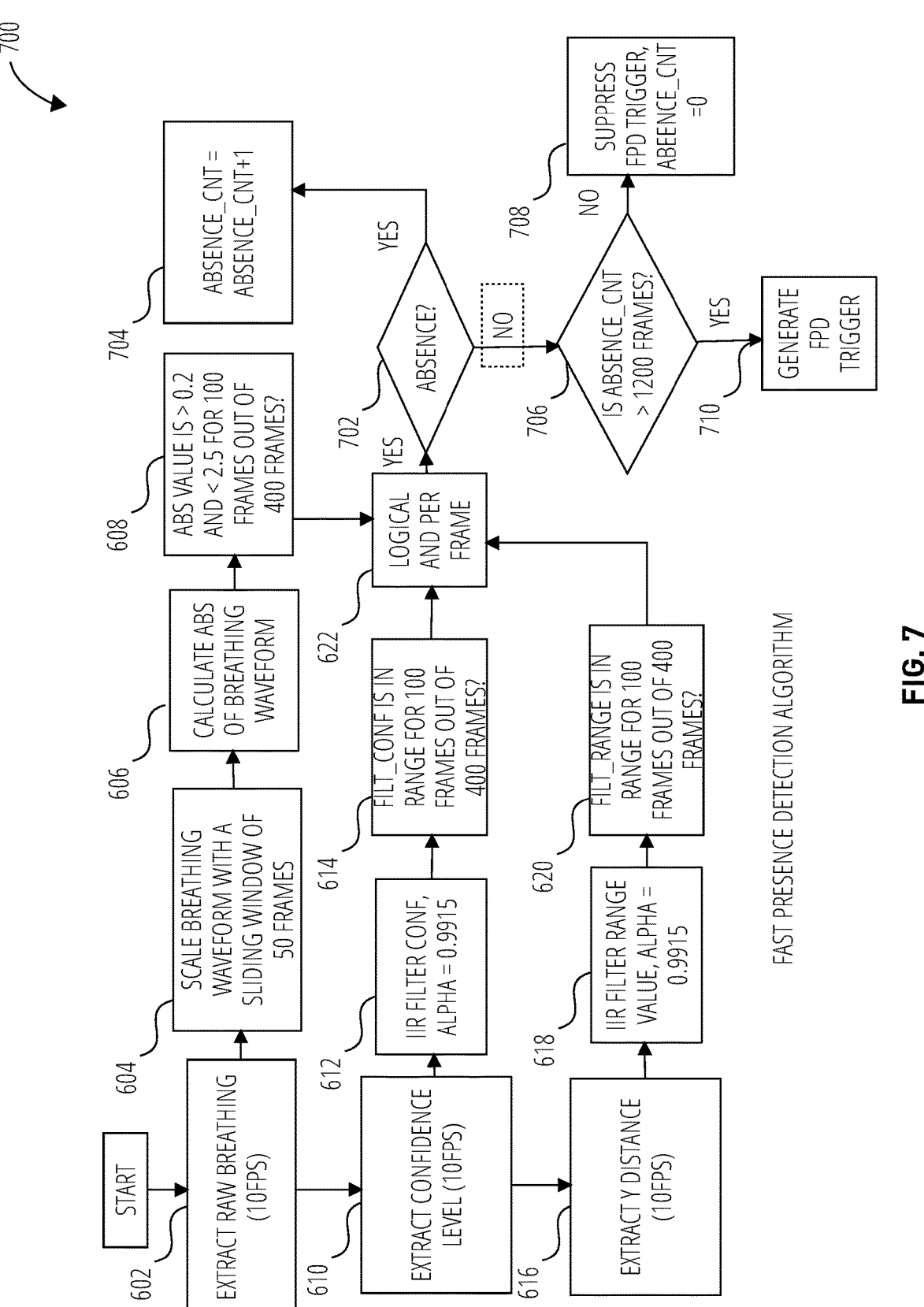
FIG. 7 is a flow diagram of an FPD process according to at least one embodiment.

FIG. 7 is a flow diagram of an FPD process 700 according to at least one embodiment. The FPD process 700 may be performed, at least in part, by processing logic that may include hardware (e.g., circuitry, dedicated logic, programmable logic, microcode, processing device, etc.), software (such as instructions run on a processing device, a general-purpose computer system, or a dedicated machine), firmware, microcode, or a combination thereof. The FPD process 600 may be implemented, for example, by the sleep-monitoring device 106. The FPD process 700 may be implemented, for example, by one or more server(s) 120 hosting the FPD processing logic 134 in connection with the sleep-monitoring device 106 with the radar unit 104.

The FPD process 700 is similar to FPD process 600 as noted by similar reference numbers, except the FPD process 700 determines whether at block 622 there is a presence or absence of the user in the first region (block 702). If the absence is detected at block 702, the processing logic increments a fourth count of data frames where the first count does not exceed the first threshold at block 608, the second count does not exceed the second threshold at block 622, or the third count does not exceed the third threshold at block 620. When the presence is detected at block 702, the processing logic determines if the fourth count exceeds a fourth threshold (e.g., absence_cnt>1200 frames) (block 706). If not, the processing logic suppresses or otherwise prevents an FPD trigger of an event and can reset the fourth count. If the fourth count exceeds the fourth threshold at block 706, the processing logic generates the FPD trigger of the event (block 710).

For example, in a case where the person enters the bed and lies in bed for 1 minute in a natural position, the different metrics and the calculated FPD trigger with respect to ground truth data are shown in FIG. 8.

FIG. 8 is a graph 800 illustrating FPD detection with respect to ground truth data according to at least one embodiment. Graph 800 shows ground truth data with an event 802 where the user enters and lies in bed for a period (e.g., 1 minute). As described herein, the FPD algorithm 400 uses breathing waveform information 806, confidence level information 808 (e.g., IIR confidence values), and range information 810 (e.g., IIR range values) to detect an FPD event 804. As described herein, the FPD event 804 can be detected within 65 seconds or less of the event 802.

As described above, a breathing waveform can be scaled to compensate for a moving DC offset, as illustrated in FIG. 9.

FIG. 9 is a graph 900 illustrating the scaling of breathing waveform according to at least one embodiment. The graph 900 shows a raw breathing waveform 902 over a period of time. The raw breathing waveform 902 can include a moving DC offset. The processing logic can scale the raw breathing waveform 902 with a sliding window 908 of a set number of frames (e.g., 50 frames) to obtain a scaled breathing waveform 904. The processing logic can also determine the absolute magnitude values of the scaled breathing waveform 904 to obtain absolute breathing waveform 906 (e.g., peak-to-peak). The scaled breathing waveform 904 and absolute breathing waveform 906 remove the DC offset from the breathing waveform. As described above, the absolute magnitude values can be used with confidence level information 808 (e.g., IIR confidence values) and range information 810 (e.g., IIR range values) to detect an FPD event 804.

Figure 10:
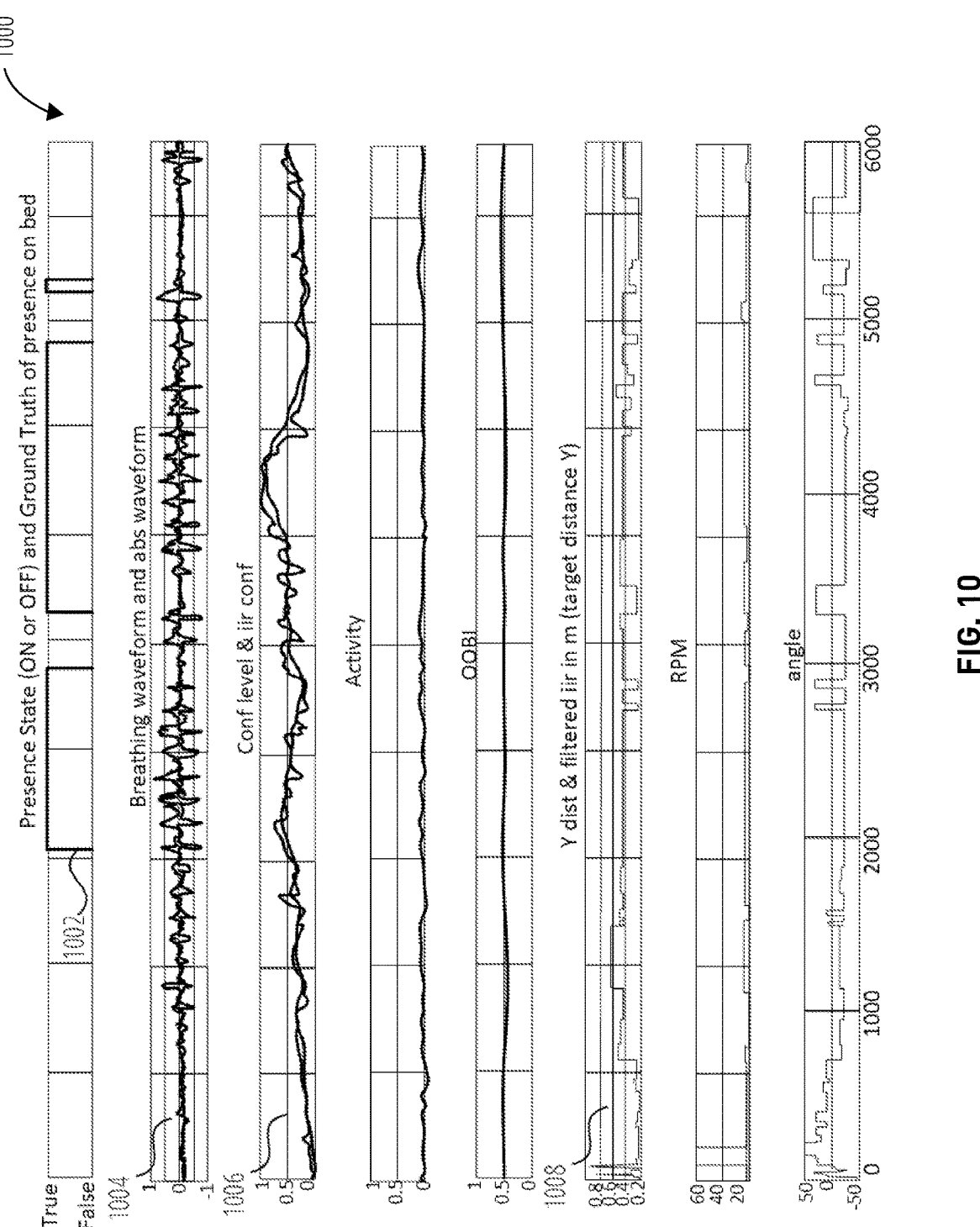
FIG. 10 is a graph illustrating a fan causing presence detection according to at least one embodiment.

In some cases, non-human objects, such as fans, can create data that represents a breathing waveform, such as illustrated in FIG. 10.

FIG. 10 is a graph 1000 illustrating a fan causing presence detection according to at least one embodiment. Graph 1000 shows ground truth data without any event where the user enters the bed. As described herein, the FPD algorithm 400 uses breathing waveform information 1004, confidence level information 1006 (e.g., IIR confidence values), and range information 1008 (e.g., IIR range values) to detect an FPD event 1002. The FPD event 1002, however, is not accurate. One of the reasons for this could be that a fan is causing a bedsheet or a pillow cover to move, which is then detected by the radar unit. The confidence level information 1006 and range information 1008 do not necessarily avoid the presence detection with 100% accuracy. Even the RPM information is pretty stable. In some embodiments, an additional metric can be calculated and used in connection with the confidence level information. In at least one embodiment, the additional metric is a least squares method (LSM) metric that can be fed into the confidence level. LSM is a statistical metric used to find or estimate the numerical values of the parameters to fit a function to a set of data and to characterize the statistical properties of estimates. If the LSM value is below a threshold, the FPD event 1002 can be prohibited or mitigated. Alternatively, other metrics can be calculated to eliminate FPD triggers caused by non-human objects, such as a fan.

In some cases, people in the bedroom for non-sleep-related activities can cause errors in detection. For example, a person entering the room to pick up an object on the opposite side of the bed can trigger an FPD event without any timing input, as illustrated in FIG. 12.

Figure 11:
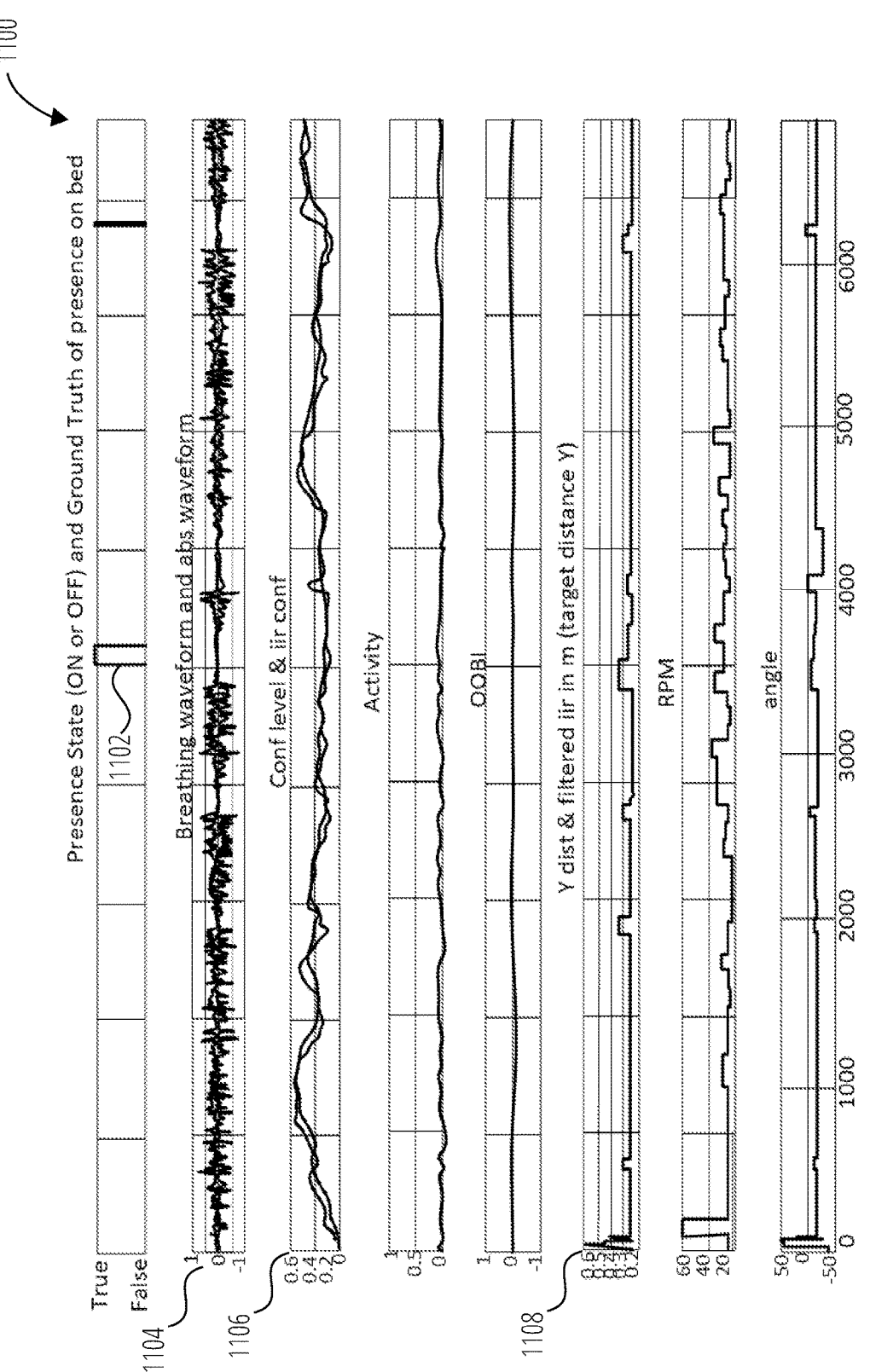
FIG. 11 is a graph illustrating entering to pick up an object on the opposite side of the bed according to at least one embodiment.

FIG. 11 is a graph 1100 illustrating entering to pick up an object on the opposite side of the bed according to at least one embodiment. Graph 1100 shows ground truth data without any event where the user enters the bed. As described herein, the FPD algorithm 400 uses breathing waveform information 1104, confidence level information 1106 (e.g., IIR confidence values), and range information 1108 (e.g., IIR range values) to detect an FPD event 1102. The FPD event 1102, however, is not accurate. One of the reasons for this could be that there is a strong breathing waveform, confidence values, and range values. In some cases, the values need to be within range for a minimum amount of time. For example, any relatively static presence above 20 seconds can trigger an FPD event, mitigating or preventing the FPD event 1102.

FIG. 12 is a flow diagram of a method 1200 for detecting an event representing a user entering a first region according to at least one embodiment. Method 1200 may be performed, at least in part, by processing logic that may include hardware (e.g., circuitry, dedicated logic, programmable logic, microcode, processing device, etc.), software (such as instructions run on a processing device, a general-purpose computer system, or a dedicated machine), firmware, microcode, or a combination thereof. The method 1200 can be implemented by the sleep-monitoring device 106. Method 1200 may be implemented, for example, by one or more server(s) 120 hosting the FPD processing logic 134 in connection with the sleep-monitoring device 106 with the radar unit 104.

The method 1200 begins with the processing logic receiving radar data from radar unit of a sleep-monitoring device (block 1202). The radar data includes i) first data representing a breathing waveform associated with a user located in an environment around the sleep-monitoring device, ii) a first set of range values, each range value representing a physical distance between the user and the radar unit, and iii) a first set of confidence values associated with the first data. At block 1204, the processing logic determines absolute magnitude values using the first data. At block 1206, the processing logic determines first infinite impulse response (IIR) values using the first set of range values. At block

1208, the processing logic determines second IIR values using the first set of confidence values. At block 1210, the processing logic determines a first event representing the user located in a first region of the environment using the absolute magnitude values, the first IIR values, and the second IIR values. At block 1212, the processing logic sends an indication of the first event to a cloud service that causes one or more devices in the environment to perform one or more actions.

In a further embodiment, the processing logic receives second radar data from the radar unit corresponding to a second period after a first period. The second radar data includes i) third data representing the breathing waveform associated with the user, ii) a second set of range values, and iii) a second set of confidence values associated with the third data. The processing logic determines second absolute magnitude values using the third data. The processing logic determines third IIR values using the second set of range values. The processing logic determines fourth IIR values using the second set of confidence values. The processing logic determines a second event representing the user exiting the first region using the second absolute magnitude values, the third IIR values, and the fourth IIR values. The processing logic sends a second indication of the second event to the cloud service that causes the one or more devices to perform one or more additional actions.

In at least one embodiment, the first event represents the user entering a bed in the first region. The one or more actions can include at least one of locking a door, activating an alarm system, turning on a television, turning off a television, dimming a light, turning off a light, changing a color of a light, playing a sleep sound using a speaker, playing a song using a speaker, or turning off a speaker.

In at least one embodiment, the processing logic determines a current time of the first event. The processing logic determines that the current time occurs outside of a time period. The processing logic prevents the indication from being sent in response to the current time occurring outside of the time period.

In at least one embodiment, the processing logic determines that the first event occurs within sixty-five seconds or less from the user being located in the first region.

In at least one embodiment, the radar data includes a set of data frames, each data frame of the set of the data frames comprises i) one of the absolute magnitude values, ii) one of the first IIR values, and iii) one of the second IIR values. The processing logic determines a first count of data frames in the set of data frames including an absolute magnitude value that satisfies a first criterion;

The processing logic determines a second count of data frames in the set of data frames including a first IIR value that satisfies a second criterion;

The processing logic determines a third count of data frames in the set of data frames including a second IIR value that satisfies a third criterion; and The processing logic determines the first event in response to the first count exceeding a first threshold, the second count exceeding a second threshold, and the third count exceeding a third threshold.

In at least one embodiment, the radar data includes a set of data frames, each data frame of the set of the data frames comprises i) one of the absolute magnitude values, ii) one of the first IIR values, and iii) one of the second IIR values. The processing logic determines a first count of data frames in the set of data frames including an absolute magnitude value that satisfies a first criterion. The processing logic determines a second count of data frames in the set of data frames including a first IIR value that satisfies a second criterion. The processing logic determines a third count of data frames in the set of data frames including a second IIR value that satisfies a third criterion. The processing logic determines a fourth count of instances where the first count does not exceed a first threshold, the second count does not exceed a second threshold, or the third count does not exceed a third threshold. The processing logic determines the first event in response to the first count exceeding the first threshold, the second count exceeding the second threshold, the third count exceeding the third threshold, and the fourth count exceeding a fourth threshold.

Figure 13:
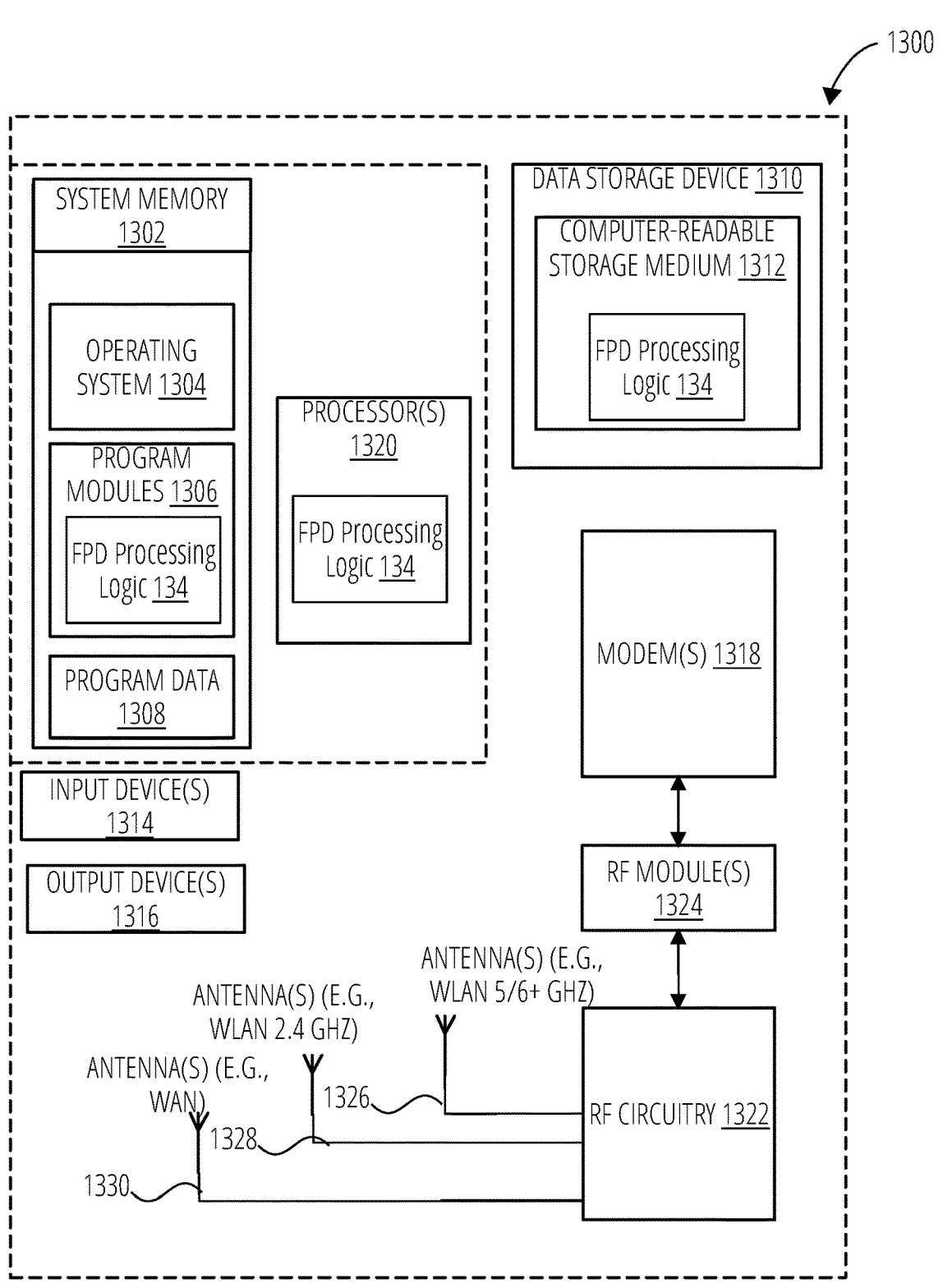
FIG. 13 is a block diagram of an electronic device with a FPD algorithm, according to at least one embodiment of the present disclosure.

FIG. 13 is a block diagram of an electronic device 1300 with FPD processing logic, according to at least one embodiment of the present disclosure. The electronic device 1300 may correspond to the user devices described herein. The electronic device 1300 includes one or more processor(s) 1320, such as one or more central processing units (CPUs), microcontrollers, field-programmable gate arrays, or other types of processors. The electronic device 1300 also includes system memory 1302, which may correspond to any combination of volatile and/or non-volatile storage mechanisms. The system memory 1302 stores information that provides operating system component 1304, various program modules 1306, program data 1308, and/or other components. The program modules 1306 may include instructions of the FPD processing logic 134. The FPD processing logic 134 can perform any of the operations described herein. In one embodiment, the system memory 1302 stores instructions of methods to control the operation of the electronic device 1300. The electronic device 1300 performs functions by using the processor(s) 1320 to execute instructions provided by the system memory 1302.

The electronic device 1300 also includes a data storage device 1310 that may be composed of one or more types of removable storage and/or one or more types of non-removable storage. The data storage device 1310 includes a computer-readable storage medium 1312 on which is stored one or more sets of instructions embodying any of the methodologies or functions described herein. Instructions for the program modules 1306 may reside, completely or at least partially, within the computer-readable storage medium 1312, system memory 1302 and/or within the processor(s) 1320 during execution thereof by the electronic device 1300, the system memory 1302, and the processor(s) 1320 also constituting computer-readable media. The electronic device 1300 may also include one or more input device(s) 1314 (keyboard, mouse device, specialized selection keys, etc.) and one or more output device(s) 1316 (displays, printers, audio output mechanisms, etc.).

The electronic device 1300 further includes a modem(s) 1318 to allow the electronic device 1300 to communicate via wireless connections (e.g., provided by the wireless communication system) with other computing devices, such as remote computers, an item-providing system, and so forth. The modem(s) 1318 can be connected to one or more radio frequency (RF) modules 1324. The RF modules 1324 may be a WLAN module, a WAN module, a personal area network (PAN) module, a GPS module, or the like. The antenna structures (antenna(s) 1326, 1328, and 1330) are coupled to the Rf circuitry 1322, which is coupled to the modem(s) 1318. The Rf circuitry 1322 may include radio front-end circuitry, antenna switching circuitry, impedance matching circuitry, or the like. In one embodiment, the Rf circuitry 1322 includes the radio frequency front-end (RFFE) circuitry with high selectivity performance as described in the various embodiments of FIG. 1 to FIG. 24.

The antennas antenna 1326 may be GPS antennas, NFC antennas, other WAN antennas, WLAN or PAN antennas, or the like. The modem(s) 1318 allows the electronic device 1300 to handle both voice and non-voice communications (such as communications for text messages, multimedia messages, media downloads, web browsing, etc.) with a wireless communication system. The modem(s) 1318 may provide network connectivity using any type of mobile network technology, including, for example, cellular digital packet data (CDPD), general packet radio service (GPRS), EDGE, universal mobile telecommunications system (UMTS), 1 times radio transmission technology (1×RTT), evaluation data optimized (EVDO), high-speed down-link packet access (HSDPA), Wi-Fi®, Long Term Evolution (LTE) and LTE Advanced (sometimes generally referred to as 4G), etc.

The modem(s) 1318 may generate signals and send these signals to antenna(s) 1326 of a first type (e.g., WLAN 5/6+ GHz), antenna(s) 1328 of a second type (e.g., WLAN 2.4 GHZ), and/or antenna(s) 1330 of a third type (e.g., WAN), via Rf circuitry 1322, and Rf module(s) 1324 as described herein. Antennas 1326, 1328, 1330 may be configured to transmit in different frequency bands and/or using different wireless communication protocols. The antennas 1326, 1328, 1330 may be directional, omnidirectional, or non-directional antennas. In addition to sending data, antennas 1326, 1328, 1330 may also receive data, which is sent to appropriate RF modules connected to the antennas. One of the antennas 1326, 1328, 1330 may be any combination of the antenna structures described herein.

In one embodiment, the electronic device 1300 establishes a first connection using a first wireless communication protocol and a second connection using a different wireless communication protocol. The first wireless connection and second wireless connection may be active concurrently, for example, if an electronic device is receiving a media item from another electronic device (e.g., a mini-POP node) via the first connection) and transferring a file to another user device (e.g., via the second connection) at the same time. Alternatively, the two connections may be active concurrently during wireless communications with multiple devices. In one embodiment, the first wireless connection is associated with a first resonant mode of an antenna structure that operates at a first frequency band. The second wireless connection is associated with a second resonant mode of the antenna structure that operates at a second frequency band. In another embodiment, the first wireless connection is associated with a first antenna structure, and the second wireless connection is associated with a second antenna.

Though a modem 1318 is shown to control transmission and reception via antenna (1326, 1328, 1330), the electronic device 1300 may alternatively include multiple modems, each of which is configured to transmit/receive data via a different antenna and/or wireless transmission protocol.

In the above description, numerous details are set forth. It will be apparent, however, to one of ordinary skill in the art having the benefit of this disclosure, that embodiments may be practiced without these specific details. In some instances, well-known structures and devices are shown in block diagram form, rather than in detail, in order to avoid obscuring the description.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "inducing," "parasitically inducing," "radiating," "detecting," "determining," "generating," "communicating," "receiving," "disabling," or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

Embodiments also relate to an apparatus for performing the operations herein. This apparatus may be specially constructed for the required purposes, or it may comprise a general-purpose computer selectively activated or reconfigured by a computer program stored in the computer. Such a computer program may be stored in a computer-readable storage medium, such as, but not limited to, any type of disk, including floppy disks, optical disks, CD-ROMs and magnetic-optical disks, read-only memories (ROMs), random access memories (RAMs), EPROMS, EEPROMs, magnetic or optical cards, or any type of media suitable for storing electronic instructions.

The algorithms and displays presented herein are not inherently related to any particular computer or other apparatus. Various general-purpose systems may be used with programs in accordance with the teachings herein, or it may prove convenient to construct a more specialized apparatus to perform the required method steps. The required structure for a variety of these systems will appear from the description below. In addition, the present embodiments are not described with reference to any particular programming language. It will be appreciated that a variety of programming languages may be used to implement the teachings of the present embodiments as described herein. It should also be noted that the terms "when" or the phrase "in response to," as used herein, should be understood to indicate that there may be intervening time, intervening events, or both before the identified operation is performed.

It is to be understood that the above description is intended to be illustrative, and not restrictive. Many other embodiments will be apparent to those of skill in the art upon reading and understanding the above description. The scope of the present embodiments should, therefore, be determined with reference to the appended claims, along with the full scope of equivalents to which such claims are entitled.

What is claimed is:

1. A computing device comprising:
    one or more processors; and
    memory to store computer-executable instructions that, if executed, cause the one or more processors to:

receive radar data from a radar unit, wherein the radar data comprises i) first data representing a breathing waveform associated with a user located in an environment around the computing device, ii) a first set of range values, each range value representing a physical distance between the user and the radar unit, and iii) a first set of confidence values associated with the first data;
    determine absolute magnitude values using the first data;
    determine first infinite impulse response (IIR) values using the first set of range values;
    determine second IIR values using the first set of confidence values;
    determine, using the absolute magnitude values, the first IIR values, and the second IIR values, a first event, the first event representing the user being present in a first region of the environment; and
    send an indication of the first event to a cloud service that causes one or more devices in the environment to perform one or more actions.

2. The computing device of claim 1, wherein the memory to store computer-executable instructions that, if executed, further cause the one or more processors to:
    receive second radar data from the radar unit corresponding to a second period after a first period, wherein the second radar data comprises i) third data representing the breathing waveform associated with the user, ii) a second set of range values, and iii) a second set of confidence values associated with the third data;
    determine second absolute magnitude values using the third data;
    determine third IIR values using the second set of range values;
    determine fourth IIR values using the second set of confidence values;
    determine, using the second absolute magnitude values, the third IIR values, and the fourth IIR values, a second event representing the user exiting the first region; and
    send a second indication of the second event to the cloud service that causes the one or more devices to perform one or more additional actions.

3. The computing device of claim 1, wherein the one or more devices comprises a light, a speaker, a lock, an alarm system, or a television, wherein the first event represents the user entering a bed in the first region, and wherein the one or more actions comprises at least one of dimming the light, turning off the light, changing a color of the light, playing a sleep sound using the speaker, playing a song using the speaker, turning off the speaker, locking the lock, activating the alarm system, turning on the television, or turning off the television.

4. The computing device of claim 1, wherein the memory to store computer-executable instructions that, if executed, further cause the one or more processors to:
    determine a current time of the first event;
    determine that the current time occurs outside of a time period; and
    prevent the indication from being sent.

5. The computing device of claim 1, wherein the memory to store computer-executable instructions that, if executed, further cause the one or more processors to:
    determine that the first event occurs within sixty-five seconds or less from the user entering the first region.

6. The computing device of claim 1, wherein the radar data comprises a set of data frames, each data frame of the set of the data frames comprises i) one of the absolute magnitude values, ii) one of the first IIR values, and iii) one of the second IIR values, wherein the memory to store computer-executable instructions that, if executed, further cause the one or more processors to:

determine a first count of data frames in the set of data frames including an absolute magnitude value that satisfies a first criterion;

determine a second count of data frames in the set of data frames including a first IIR value that satisfies a second criterion;

determine a third count of data frames in the set of data frames including a second IIR value that satisfies a third criterion; and determine the first event in response to the first count exceeding a first threshold, the second count exceeding a second threshold, and the third count exceeding a third threshold.

7. The computing device of claim 1, wherein the radar data comprises a set of data frames, each data frame of the set of the data frames comprises i) one of the absolute magnitude values, ii) one of the first IIR values, and iii) one of the second IIR values, wherein to determine the first event, the computer-executable instructions further cause the one or more processors to:

determine a first count of data frames in the set of data frames including an absolute magnitude value that satisfies a first criterion;

determine a second count of data frames in the set of data frames including a first IIR value that satisfies a second criterion;

determine a third count of data frames in the set of data frames including a second IIR value that satisfies a third criterion;

determine a fourth count of instances where the first count does not exceed a first threshold, the second count does not exceed a second threshold, or the third count does not exceed a third threshold; and determine the first event in response to the first count exceeding the first threshold, the second count exceeding the second threshold, the third count exceeding the third threshold, and the fourth count exceeding a fourth threshold.

8. A method comprising:

receiving radar data from a radar unit of a sleep-monitoring device, wherein the radar data comprises i) first data representing a breathing waveform associated with a user located in an environment around the sleep-monitoring device, ii) a first set of range values, each range value representing a physical distance between the user and the radar unit, and iii) a first set of confidence values associated with the first data;

determining absolute magnitude values using the first data;

determining first infinite impulse response (IIR) values using the first set of range values;

determining second IIR values using the first set of confidence values;

determining, using the absolute magnitude values, the first IIR values, and the second IIR values, a first event, the first event representing the user being present in a first region of the environment; and sending an indication of the first event to a cloud service that causes one or more devices in the environment to perform one or more actions.

9. The method of claim 8, further comprising:

receive second radar data from the radar unit corresponding to a second period after a first period, wherein the second radar data comprises i) third data representing the breathing waveform associated with the user, ii) a second set of range values, and iii) a second set of confidence values associated with the third data;

determine second absolute magnitude values using the third data;

determine third IIR values using the second set of range values;

determine fourth IIR values using the second set of confidence values;

determine, using the second absolute magnitude values, the third IIR values, and the fourth IIR values, a second event representing the user exiting the first region; and send a second indication of the second event to the cloud service that causes the one or more devices to perform one or more additional actions.

10. The method of claim 8, wherein the one or more devices comprises a light, a speaker, a lock, an alarm system, or a television, wherein the first event represents the user entering a bed in the first region, and wherein the one or more actions comprises at least one of locking the door, activating the alarm system, turning on the television, turning off the television, dimming the light, turning off the light, changing a color of the light, playing a sleep sound using the speaker, playing a song using the speaker, or turning off the speaker.

11. The method of claim 8, further comprising:

determining a current time of the first event;

determine that the current time occurs outside of a time period; and preventing the indication from being sent.

12. The method of claim 8, further comprising determining that the first event occurs within sixty-five seconds or less from the user being located in the first region.

13. The method of claim 8, wherein the radar data comprises a set of data frames, each data frame of the set of the data frames comprises i) one of the absolute magnitude values, ii) one of the first IIR values, and iii) one of the second IIR values, and wherein the method further comprises:

determining a first count of data frames in the set of data frames including an absolute magnitude value that satisfies a first criterion;

determining a second count of data frames in the set of data frames including a first IIR value that satisfies a second criterion;

determining a third count of data frames in the set of data frames including a second IIR value that satisfies a third criterion; and determining the first event in response to the first count exceeding a first threshold, the second count exceeding a second threshold, and the third count exceeding a third threshold.

14. The method of claim 8, wherein the radar data comprises a set of data frames, each data frame of the set of the data frames comprises i) one of the absolute magnitude values, ii) one of the first IIR values, and iii) one of the second IIR values, and wherein the method further comprises:

determining a first count of data frames in the set of data frames including an absolute magnitude value that satisfies a first criterion;

determining a second count of data frames in the set of data frames including a first IIR value that satisfies a second criterion;

determining a third count of data frames in the set of data frames including a second IIR value that satisfies a third criterion;

determining a fourth count of instances where the first count does not exceed a first threshold, the second count does not exceed a second threshold, or the third count does not exceed a third threshold; and determining the first event in response to the first count exceeding the first threshold, the second count exceeding the second threshold, the third count exceeding the third threshold, and the fourth count exceeding a fourth threshold.

15. A sleep-monitoring device comprising:

a radar unit; and a computing device coupled to the radar unit, wherein the computing device is configured to:

receive radar data from the radar unit, wherein the radar data comprises i) first data representing a breathing waveform associated with a user located in an environment around the computing device, ii) a first set of range values, each range value representing a physical distance between the user and the radar unit, and iii) a first set of confidence values associated with the first data;

determine absolute magnitude values using the first data;

determine first infinite impulse response (IIR) values using the first set of range values;

determine second IIR values using the first set of confidence values;

determine, using the absolute magnitude values, the first IIR values, and the second IIR values, a first event, the first event representing the user being present in a first region of the environment; and send an indication of the first event to a cloud service that causes one or more devices in the environment to perform one or more actions.

16. The sleep-monitoring device of claim 15, wherein the computing device is further to:

receive second radar data from the radar unit corresponding to a second period after a first period, wherein the second radar data comprises i) third data representing the breathing waveform associated with the user, ii) a second set of range values, and iii) a second set of confidence values associated with the third data;

determine second absolute magnitude values using the third data;

determine third IIR values using the second set of range values;

determine fourth IIR values using the second set of confidence values;

determine, using the second absolute magnitude values, the third IIR values, and the fourth IIR values, a second event representing the user exiting the first region; and send a second indication of the second event to the cloud service that causes the one or more devices to perform one or more additional actions.

17. The sleep-monitoring device of claim 15, wherein the one or more devices comprises a light, a speaker, a lock, an alarm system, or a television, wherein the first event represents the user entering a bed in the first region, wherein the one or more actions comprises at least one of locking the lock, activating the alarm system, turning on the television, turning off the television, dimming the light, turning off the light, changing a color of the light, playing a sleep sound using the speaker, playing a song using the speaker, or turning off the speaker.

18. The sleep-monitoring device of claim 15, wherein the computing device is further to:

determine a current time of the first event;

determine that the current time occurs outside of a time period; and prevent the indication from being sent.

19. The sleep-monitoring device of claim 15, wherein the computing device is further to determine that the first event occurs within a window of sixty-five seconds or less from the user entering the first region.

20. The sleep-monitoring device of claim 15, wherein the radar data comprises a set of data frames, each data frame of the set of the data frames comprises i) one of the absolute magnitude values, ii) one of the first IIR values, and iii) one of the second IIR values, wherein the computing device is further to:

determine a first count of data frames in the set of data frames having including an absolute magnitude value that satisfies a first criterion;

determine a second count of data frames in the set of data frames having including a first IIR value that satisfies a second criterion;

determine a third count of data frames in the set of data frames having including a second IIR value that satisfies a third criterion; and determine the first event in response to the first count exceeding a first threshold, the second count exceeding a second threshold, and the third count exceeding a third threshold.

* * * * *